United States Patent
Tsurumi

(10) Patent No.: US 10,817,053 B2
(45) Date of Patent: Oct. 27, 2020

(54) INFORMATION PROCESSING APPARATUS AND INFORMATION PROCESSING METHOD

(71) Applicant: SONY CORPORATION, Tokyo (JP)

(72) Inventor: Shingo Tsurumi, Saitama (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/085,216

(22) PCT Filed: Dec. 22, 2016

(86) PCT No.: PCT/JP2016/088300
§ 371 (c)(1),
(2) Date: Sep. 14, 2018

(87) PCT Pub. No.: WO2017/163516
PCT Pub. Date: Sep. 28, 2017

(65) Prior Publication Data
US 2019/0079581 A1    Mar. 14, 2019

(30) Foreign Application Priority Data

Mar. 23, 2016  (JP) .................................. 2016-059122

(51) Int. Cl.
| | |
|---|---|
| *G02B 27/00* | (2006.01) |
| *G06F 3/01* | (2006.01) |
| *A61B 3/113* | (2006.01) |
| *G06K 9/20* | (2006.01) |
| *G06K 9/00* | (2006.01) |

(52) U.S. Cl.
CPC .............. *G06F 3/013* (2013.01); *A61B 3/113* (2013.01); *G02B 27/0093* (2013.01); *G06K 9/00597* (2013.01); *G06K 9/00604* (2013.01); *G06K 9/209* (2013.01)

(58) Field of Classification Search
CPC ...................... G02B 27/0093; G06K 9/00597; G06F 3/013; A61B 3/113
See application file for complete search history.

(56) References Cited

U.S. PATENT DOCUMENTS

| | | | |
|---|---|---|---|
| 9,622,654 B2* | 4/2017 | Lawrenson | A61B 3/0025 |
| 2009/0275929 A1* | 11/2009 | Zickler | A61B 3/113 |
| | | | 606/5 |
| 2011/0170061 A1* | 7/2011 | Gordon | A61B 3/113 |
| | | | 351/206 |
| 2015/0242680 A1* | 8/2015 | Thukral | G06K 9/00335 |
| | | | 348/78 |
| 2017/0115483 A1* | 4/2017 | Aleem | G02B 27/0093 |

FOREIGN PATENT DOCUMENTS

| | | |
|---|---|---|
| JP | 2005-287782 A | 10/2005 |
| JP | 2011-224213 A | 11/2011 |

OTHER PUBLICATIONS

International Search Report and Written Opinion of PCT Application No. PCT/JP2016/088300, dated Mar. 21, 2017, 08 pages of ISRWO.

* cited by examiner

*Primary Examiner* — Clayton E. LaBalle
*Assistant Examiner* — Dennis Hancock
(74) *Attorney, Agent, or Firm* — Chip Law Group

(57) ABSTRACT

Provided is an information processing apparatus including a processing unit that detects a gaze of a gaze-detection subject on a basis of a polarization image in which an eye of the detection object is imaged.

18 Claims, 17 Drawing Sheets

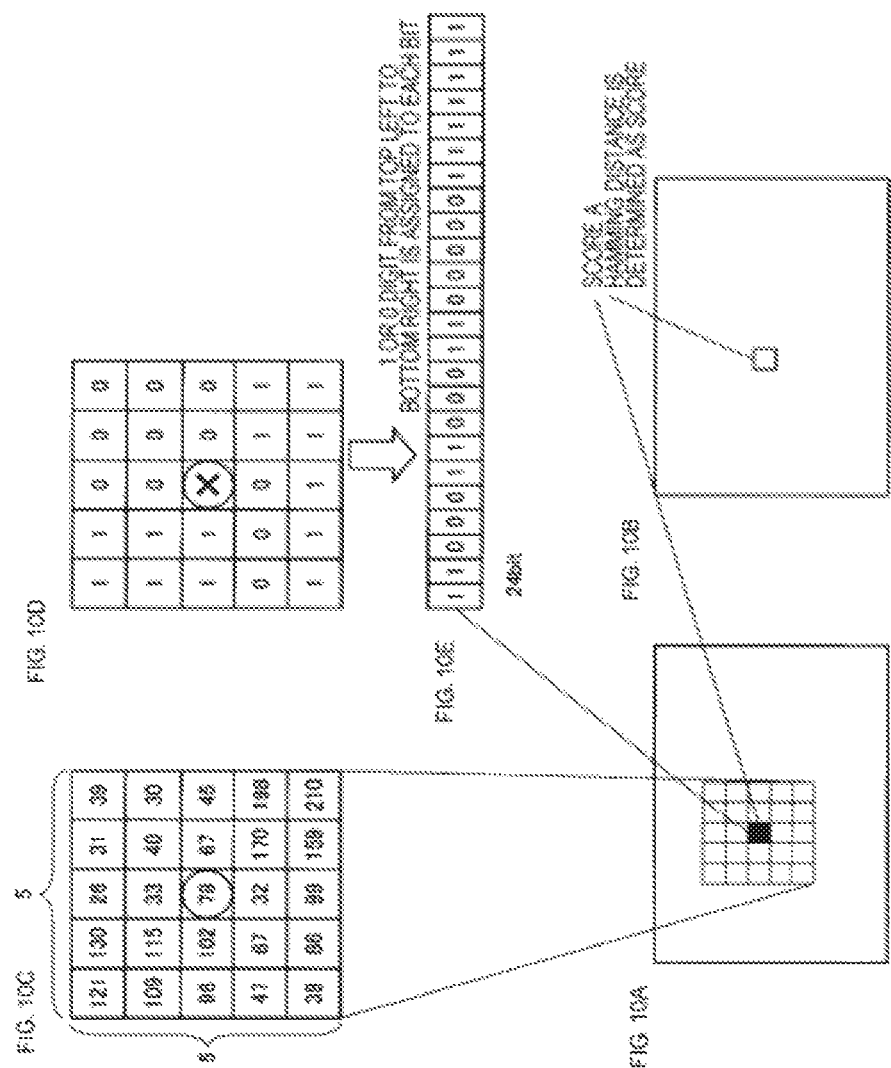

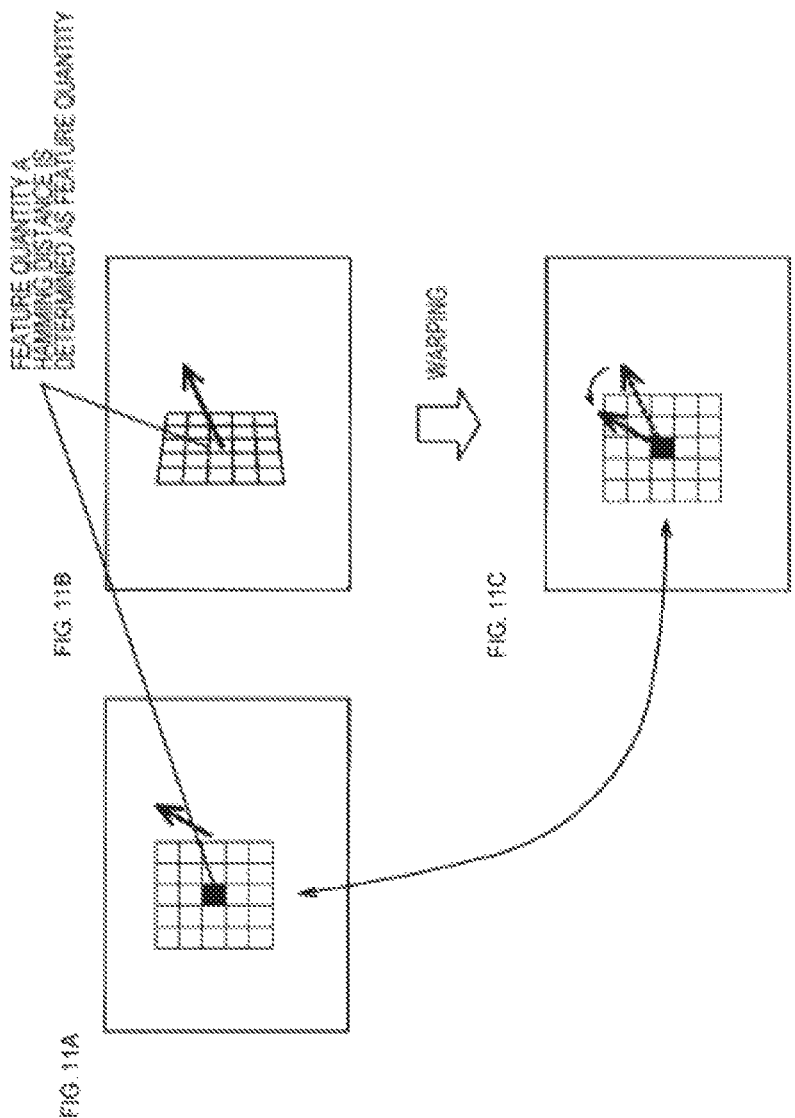

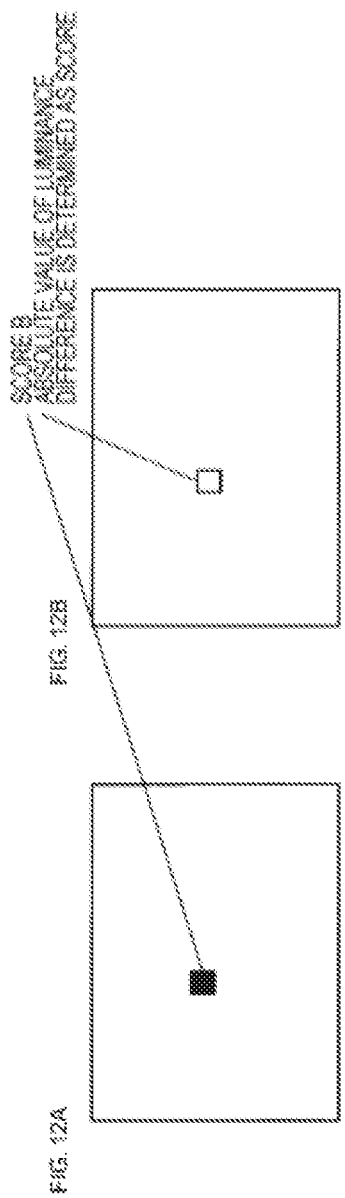

SCORE C:
LARGER VALUE OF INNER PRODUCTS
OF L_Normal 1 AND R_Normal 1 AND
L_Normal 1 and R_Normal 2, IS DETERMINED
AS SCORE

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2016/088300 filed on Dec. 22, 2016, which claims priority benefit of Japanese Patent Application No. JP 2016-059122 filed in the Japan Patent Office on Mar. 23, 2016. Each of the above-referenced applications is hereby incorporated herein by reference in its entirety.

TECHNICAL FIELD

The present disclosure relates to an information processing apparatus, an information processing method, and a program.

BACKGROUND ART

A technique for estimating a normal direction vector of an imaging object on the basis of a polarization image has been developed. For example, a technique described in Patent literature 1 below can be mentioned as a technique for estimating the normal direction vector of the imaging subject on the basis of a plurality of the polarization images imaged from different imaging positions.

CITATION LIST

Patent Literature

Patent Literature 1: WO 2009/147814

DISCLOSURE OF INVENTION

Technical Problem

Examples of a method used for detecting the gaze includes a corneal reflection method that uses a corneal reflection image (also referred to as a "Purkinje image", hereinafter the corneal reflection image may be referred to as the "Purkinje image" or a "bright point") in which light from a light source such as an infrared light emitting diode (IR LED) is reflected on the cornea). In a case of using the corneal reflection method, for example, a three-dimensional position of a cornea center in the eye can be obtained by imaging two Purkinje images with an imaging device and observing the two Purkinje images. Thus, using the corneal reflection method makes it possible to detect the gaze of a gaze-detection subject (hereinafter, also referred to simply as a "detection object") such as a person and an animal.

However, using the corneal reflection method requires light from a light source such as the IR LED and thus may cause the following issues.

- Detection accuracy of the gaze depends on how stably the Purkinje image is observed.
- Light from a light source such as the IR LED is easily affected by sunlight, causing risk of decreasing the detection accuracy of the gaze, for example, in an outdoor application.
- Using light from a light source such as the IR LED may pose a limitation on an estimation angle of the gaze.
- Requirement of installation of a light source such as the IR LED may restrict a device design.

The present disclosure proposes a novel and improved information processing apparatus, information processing method, and program, capable of detecting the gaze of a gaze-detection subject.

Solution to Problem

According to the present disclosure, there is provided an information processing apparatus including a processing unit that detects a gaze of a gaze-detection subject on a basis of a polarization image in which an eye of the detection object is imaged.

In addition, according to the present disclosure, there is provided an information processing method that is executed by an information processing apparatus, including a step of detecting a gaze of a gaze-detection subject on a basis of a polarization image in which an eye of the detection object is imaged.

In addition, according to the present disclosure, there is provided a program that causes a computer to achieve a function of detecting a gaze of a gaze-detection subject on a basis of a polarization image in which an eye of the detection object is imaged.

Advantageous Effects of Invention

According to the present disclosure, the gaze of a gaze-detection subject can be detected.

Note that the effects described above are not necessarily limitative. With or in the place of the above effects, there may be achieved any one of the effects described in this specification or other effects that may be grasped from this specification.

BRIEF DESCRIPTION OF DRAWINGS

FIGS. 10A, 10B, 10C, 10D, and 10E are illustrations that explains an example of a calculation method of a feature quantity for matching according to the present embodiment.

FIGS. 11A, 11B, and 11C are illustrations that explains an example of a calculation method of a feature quantity for matching according to the present embodiment.

FIGS. 12A and 12B are illustrations that explains an example of a calculation method of a feature quantity for matching according to the present embodiment.

FIGS. 13A and 13B are illustrations that explains an example of a calculation method of a feature quantity for matching according to the present embodiment.

MODE(S) FOR CARRYING OUT THE INVENTION

Figure 1A:
FIGS. 1A and 1B are illustrations that explains an information processing method according to the present embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, the description will be provided below in the following order.

1. An information processing method according to the present embodiment.
2. An information processing apparatus according to the present embodiment.
3. A program according to the present embodiment.

(An Information Processing Method According to the Present Embodiment)

First, an information processing method according to the present embodiment will be described. The following describes an example in which processes of the information processing method according to the present embodiment are performed by an information processing apparatus according to the present embodiment.

[1] An Outline of the Information Processing Method According to the Present Embodiment As described above, detecting the gaze using the corneal reflection method may cause various issues due to the use of light from a light source such as the IR LED.

As a measure against these issues, the information processing apparatus according to the present embodiment detects the gaze of a detection object on the basis of a polarization image in which the eye of the gaze-detection subject is imaged (detection processes). As described below, the information processing apparatus according to the present embodiment estimates a center position of the cornea in the eye on the basis of the polarization image to detect the gaze of the detection object. As described below, the center position of the cornea is estimated on the basis of a position of the pupil in the eye detected on the basis of the polarization image, and the polarization image.

More specifically, the information processing apparatus according to the present embodiment detects the gaze of the detection object on the basis of a normal line obtained from the polarization image.

The polarization image according to the present embodiment is an image imaged with an imaging device using a polarization imaging technique.

Figure 1B:
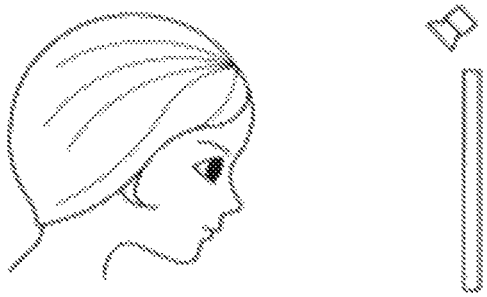

FIGS. 1A and 1B are illustrations that explains the information processing method according to the present embodiment, showing an application example of the information processing method according to the present embodiment.

FIG. 1A shows an example in which the imaging device is arranged in a wearable device that is used by mounting on the head of the detection object. That is, FIG. 1A shows an example in which the imaging device is fixed in a predetermined position with respect to the detection object. In the example shown in FIG. 1A, the information processing apparatus according to the present embodiment acquires the polarization image from such an imaging device. Examples of the wearable device used by mounting on the head of the detection object include an eye-glasses type wearable device (an eyewear) as shown in FIG. 1A, a head mounted display (HMD), and the like. Further, in the example shown in FIG. 1A, a display screen of a display device arranged in the wearable device displays various images (a still image or a moving image) such as an image related to user interface (UI).

FIG. 1B shows an example in which the imaging device is arranged in an environment. Further, in the example shown in FIG. 1B, the display screen of the display device arranged in the environment displays various images. That is, FIG. 1B shows an example in which the imaging device is fixed in a predetermined position with respect to the display device. In the example shown in FIG. 1B, the information processing apparatus according to the present embodiment acquires the polarization image from such an imaging device.

The following describes a case in which the detection object is a person as shown in FIGS. 1A and 1B as an example.

Further, in an application example shown in FIGS. 1A and 1B, examples of the information processing apparatus according to the present embodiment include a wearable device as shown in FIG. 1A, a display device as shown in FIG. 1B, a computer such as a personal computer (PC) and a server, and the like. Note that the information processing apparatus according to the present embodiment is not limited to the above examples. Other application examples of the information processing apparatus according to the present embodiment will be described below.

The polarization image is obtained, for example, by imaging with an imaging device arranged in a wearable device as shown in FIG. 1A or imaging with an imaging device arranged in an environment as shown in FIG. 1B.

Note that the imaging device according to the present embodiment may be a stereo camera that images a stereo image. In the case where the imaging device according to the present embodiment is the stereo camera, imaging with the stereo camera can obtain two polarization images that constitute the stereo image, namely, a first polarization image corresponding to a right-eye image (or a first polarization image corresponding to a left-eye image) and a second polarization image corresponding to a left-eye image (or a second polarization image corresponding to a right-eye image).

The polarization image is obtained, for example, by "installing a polarizer in front of a lens (on an imaging object side as seen from the lens) of the imaging device and imaging multiple times while rotating the installed polarizer", "arranging a polarization filter having a different polarization angle on each pixel of the imaging device and imaging once", or the like.

Figure 2:
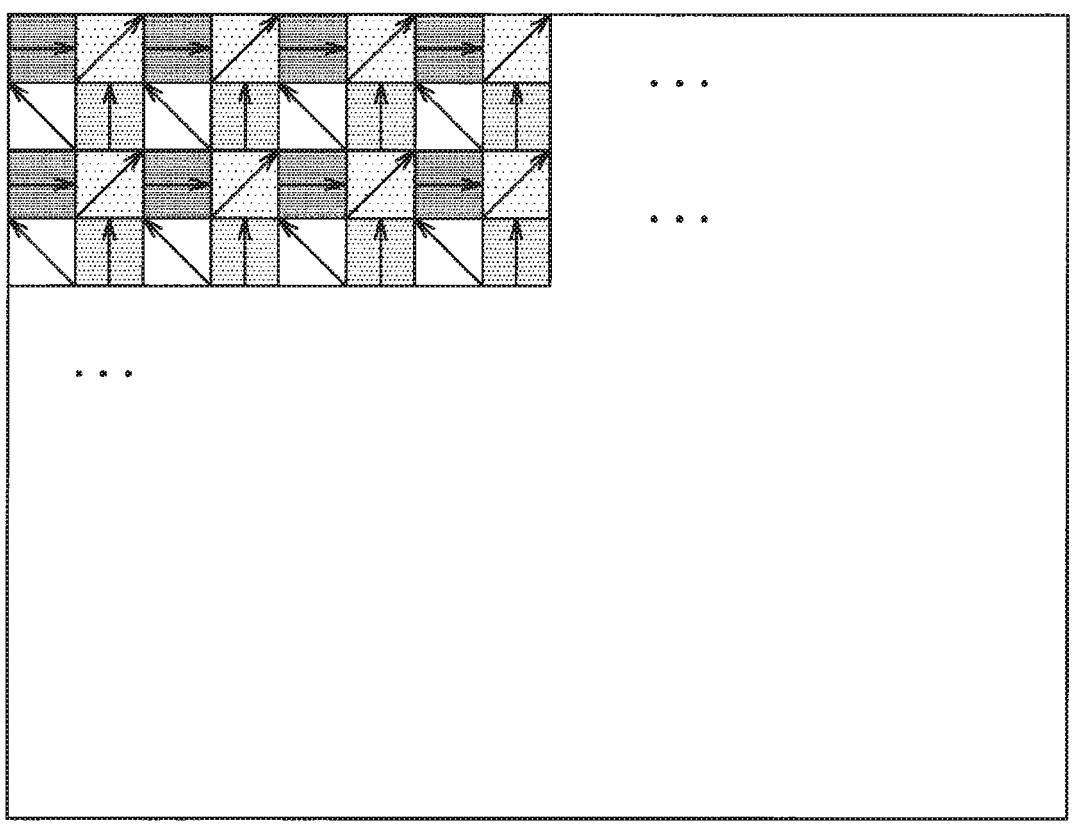
FIG. 2 is an illustration that explains an example of a method of acquiring a polarization image according to the present embodiment.

FIG. 2 is an illustration that explains an example of a method of acquiring the polarization image according to the present embodiment, showing an example of the polarization filters each arranged to a corresponding pixel of the imaging device. FIG. 2 shows an example in which the polarization filters having four different polarization angles of 0 [degrees], 45 [degrees], 90 [degrees], and 135 [degrees] are each arranged to the corresponding pixel.

The imaging device generates the polarization images, for example, by imaging through the multiple polarization filters having the different polarization angles as shown in FIG. 2. Note that, needless to say, the example of the polarization filter according to the present embodiment is not limited to the one shown in FIG. 2, and the method of acquiring the polarization image is not limited to the one using the polarization filter.

The information processing apparatus according to the present embodiment obtains normal lines, for example, on the basis of the polarization images obtained by imaging through the multiple polarization filters as shown in FIG. 2. The information processing apparatus according to the present embodiment obtains the normal lines, for example, by performing fitting of light intensities indicated by the polarization images (light intensities obtained through the multiple polarization filters) with a cosine curve and specifying a normal vector in each pixel.

Further, the information processing apparatus according to the present embodiment can obtain a luminance image (or an RGB image in a case of further using an RGB filter, the same hereinafter), for example, by averaging the polarization images imaged through the multiple polarization filters.

The normal vector in each pixel described herein is represented by an azimuth angle and a zenith angle.

Figure 3:
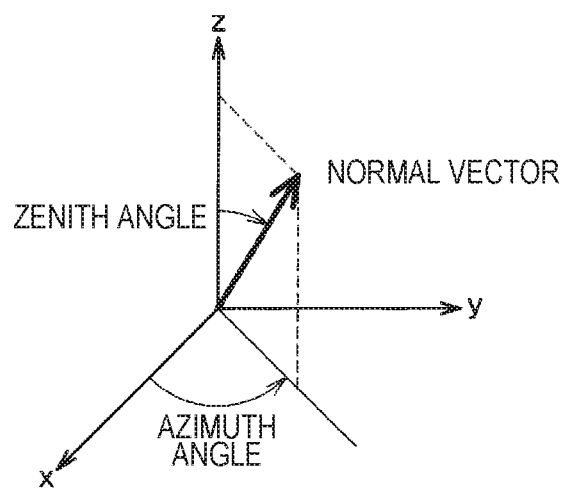
FIG. 3 is an illustration that explains the information processing method according to the present embodiment.

FIG. 3 is an illustration that explains the information processing method according to the present embodiment, showing an example of the azimuth angle and zenith angle corresponding to the normal vector.

The azimuth angle can be calculated from a phase of the cosine curve, while the zenith angle can be calculated from an amplitude of the cosine curve.

The azimuth angle described herein has an ambiguity of 180 [degrees]. Thus, there is a case where the normal vector may not be uniquely specified in some position of the imaging object.

Figure 4:
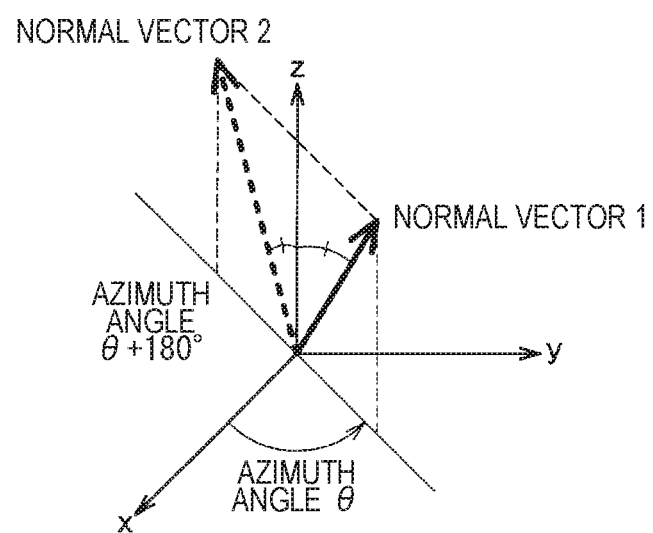
FIG. 4 is an illustration that explains the information processing method according to the present embodiment.

FIG. 4 is an illustration that explains the information processing method according to the present embodiment, showing an example in which the normal vector is not uniquely specified due to the ambiguity of the azimuth angle.

As shown in FIG. 4, the azimuth angle having the ambiguity of 180 [degrees] gives two normal vectors, a normal vector 1 and a normal vector 2, representing case where the normal vector cannot be uniquely specified in some position of the imaging object.

In the detection processes of the information processing method according to the present embodiment, as described below, the normal line on a surface of the cornea (hereinafter referred to as a "normal line corresponding to the cornea") in the eye of the detection object is obtained to detect the gaze of the detection object on the basis of the polarization image. In the processes, the eye of the detection object is known to have a spherical shape (or regarded as having a spherical shape), thus detecting a position of the pupil on the luminance image obtained from the polarization image can resolve the above-mentioned ambiguity as shown in FIG. 4. That is, the information processing apparatus according to the present embodiment specifies the normal line corresponding to the cornea from a plurality of the normal lines obtained from the polarization image on the basis of the detected position of the pupil in the eye. Further, the information processing apparatus according to the present embodiment estimates the normal line corresponding to the cornea on the basis of the detected position of the pupil in the eye and the shape of the cornea.

As described above, the information processing apparatus according to the present embodiment can obtain the normal line corresponding to the cornea in the eye of the detection object on the basis of the polarization image obtained by using a polarization imaging technique.

The information processing apparatus according to the present embodiment estimates the center position of the cornea in the eye of the detection object on the basis of the normal line obtained from the polarization image. The information processing apparatus according to the present embodiment estimates the center position of the cornea in the eye, for example, on the basis of the normal line corresponding to the cornea thus obtained.

Similarly to using the corneal reflection method, the gaze of the detection object can be detected by estimating the center position of the cornea in the eye.

In the processes, the information processing apparatus according to the present embodiment estimates the center position of the cornea on the basis of the normal line corresponding to the cornea obtained on the basis of the polarization image. That is, the information processing apparatus according to the present embodiment does not need to use the Purkinje image to estimate the center position of the cornea as is the case with the corneal reflection method.

Thus, the information processing apparatus according to the present embodiment can detect the gaze of the detection object by performing the detection processes as the processes of the information processing method according to the present embodiment without having the issues which may be caused when the corneal reflection method is used to detect the gaze.

Further, in a case where the imaging device according to the present embodiment is a stereo camera, the information processing apparatus according to the present embodiment detects the gaze of the detection object on the basis of the normal lines obtained from a first polarization image and a second polarization image constituting a stereo image. As described below, the information processing apparatus according to the present embodiment estimates the center position of the cornea in the eye of the detection object on the basis of the normal lines obtained from the first polarization image and the second polarization image to detect the gaze of the detection object.

Thus, even in the case where the information processing apparatus according to the present embodiment performs the detection processes on the basis of the first polarization image and the second polarization image constituting the stereo image, the gaze of the detection object can be detected without having the issues which may be caused when the corneal reflection method is used to detect the gaze.

[2] An Example of the Processes of Information Processing Method According to the Present Embodiment The information processing apparatus according to the present embodiment performs the "detection processes that detect the gaze of the detection object on the basis of the normal line obtained from the polarization image".

As describe above, the information processing apparatus according to the present embodiment estimates the center position of the cornea in the eye on the basis of the normal line obtained from the polarization image to detect the gaze of the detection object. The information processing apparatus according to the present embodiment estimates the center position of the cornea on the basis of the normal line corresponding to the cornea, which is estimated on the basis of the polarization image.

The processes of the information processing method according to the present embodiment will be more specifically described below.

Figure 5:
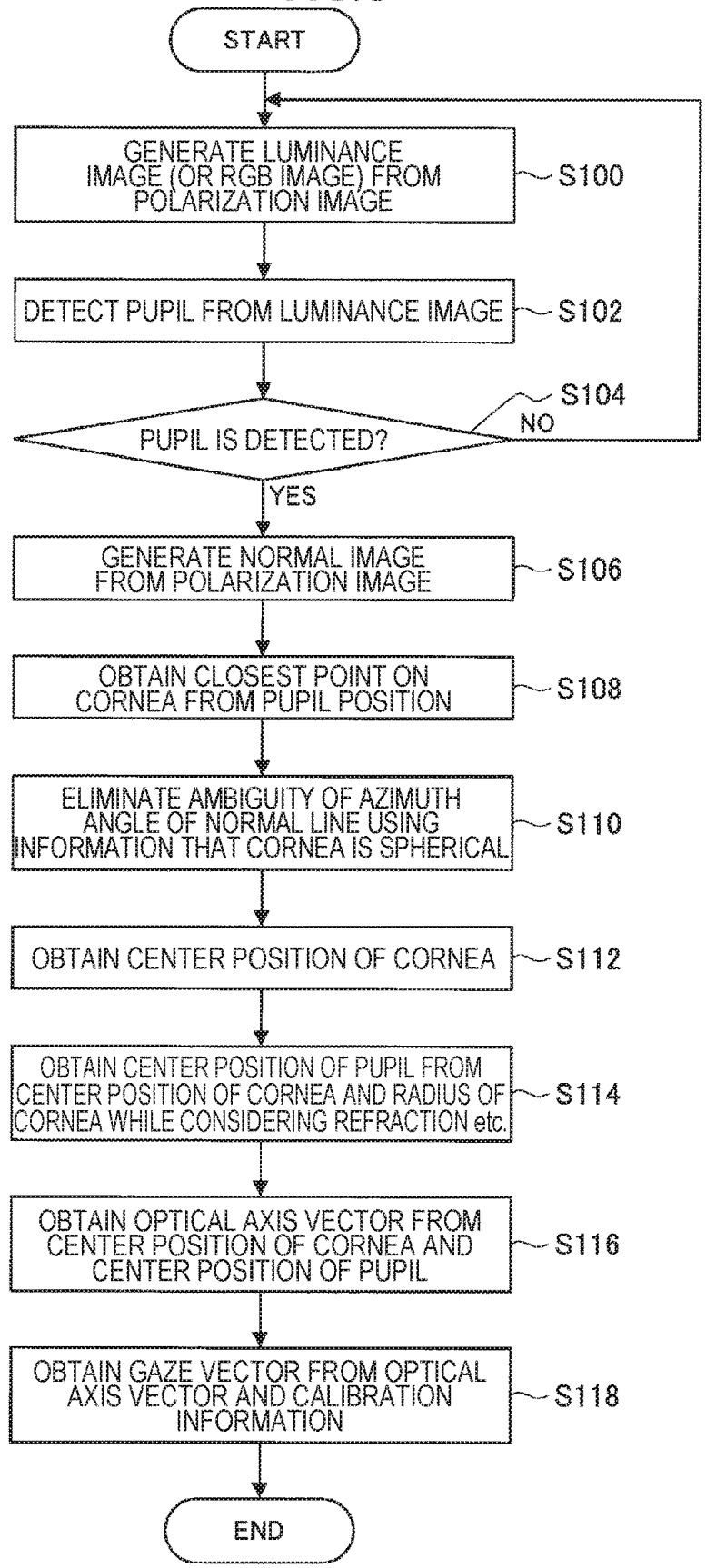
FIG. 5 is a flowchart that shows an example of processes of the information processing method according to the present embodiment.

FIG. 5 is a flowchart that shows an example of the processes of the information processing method according to the present embodiment.

The information processing apparatus according to the present embodiment generates the luminance image (or the RGB image) from the polarization image (S100). The luminance image is generated by averaging the polarization images imaged through the multiple polarization filters. Further, the information processing apparatus according to the present embodiment can generate the RGB image by further applying an RGB filter. Below, a case of generating the luminance image in the step S100 is described as an example.

The information processing apparatus according to the present embodiment detects the pupil in the eye of the detection object from the luminance image (S102). The information processing apparatus according to the present embodiment detects the pupil from the luminance image, for example, by machine learning using dictionary data for pupil detection.

The information processing apparatus according to the present embodiment determines whether the pupil is detected from the luminance image (S104). In this determination step, failing to determine that the pupil is detected from the luminance image in the step S104 corresponds to a case where the polarization image obtained by imaging with the imaging device is not the polarization images in which the eye of the detection object is imaged. Further, determining that the pupil is detected from the luminance image in the step S104 corresponds to a case where the polarization image obtained by imaging with the imaging device is the polarization images in which the eye of the detection object is imaged.

If it is not determined that the pupil is detected from the luminance image in the step S104, the information processing apparatus according to the present embodiment, for example, repeats the processes from the step S100.

Further, if it is determined that the pupil is detected from the luminance image in the step S104, the information processing apparatus according to the present embodiment, for example, generates a normal image from the polarization images (S106). The normal image is, for example, an image represented by the normal vector specified in each pixel of the polarization images. That is, the process in the step S106 corresponds to a process for obtaining the normal line in each pixel of the polarization images.

The information processing apparatus according to the present embodiment obtains the closest point on the cornea from the position of the pupil on the basis of a detection result of the pupil in the step S102 and the normal image generated in the step S106 (S108).

Figure 6:
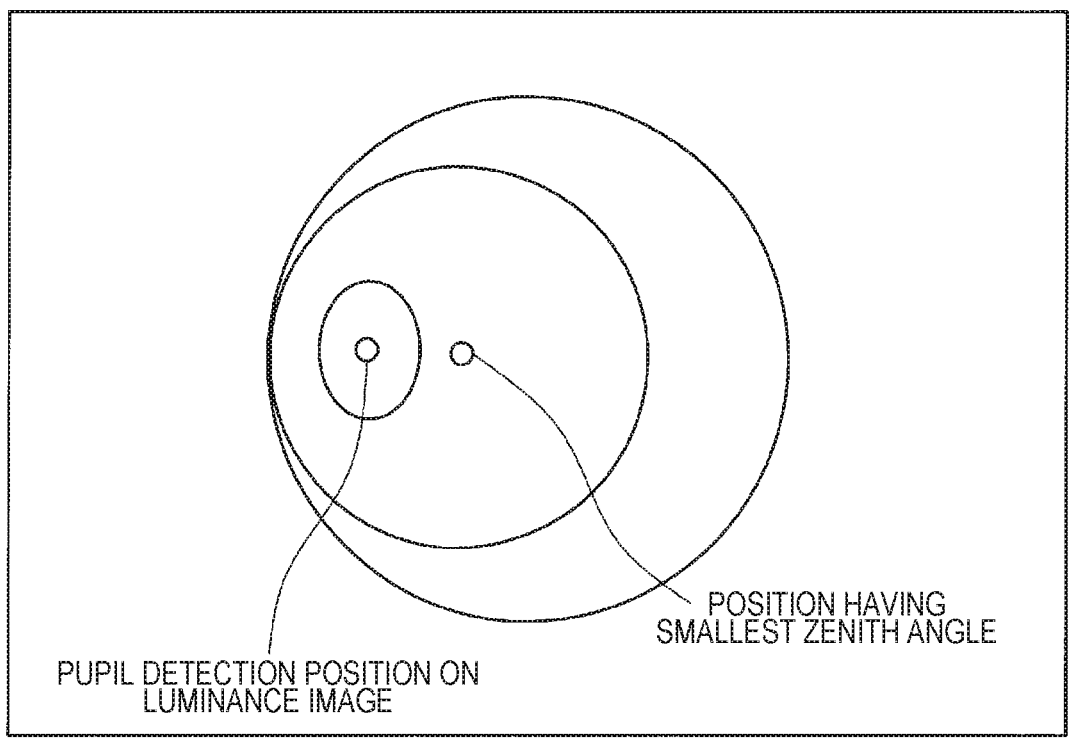
FIG. 6 is an illustration that explains an example of the processes of the information processing method according to the present embodiment.

FIG. 6 is an illustration that explains an example of the processes of the information processing method according to the present embodiment, showing an example of the closest point on the cornea. For example, as shown in FIG. 6, the closest point on the cornea is, for example, a point corresponding to a position on the cornea having the smallest zenith angle.

For example, the process in the step S108 corresponds to the process for estimating the normal line corresponding to the cornea on the basis of the position of the pupil in the eye detected on the basis of the polarization image, and the normal line obtained from the polarization image.

The information processing apparatus according to the present embodiment eliminates the ambiguity of the azimuth angle describe above on the basis of information indicating that the eye of the detection object may be regarded as spherical, that is, the cornea may be regarded as spherical (or the cornea may be regarded to have a convex spherical surface) (S110).

Figure 7:
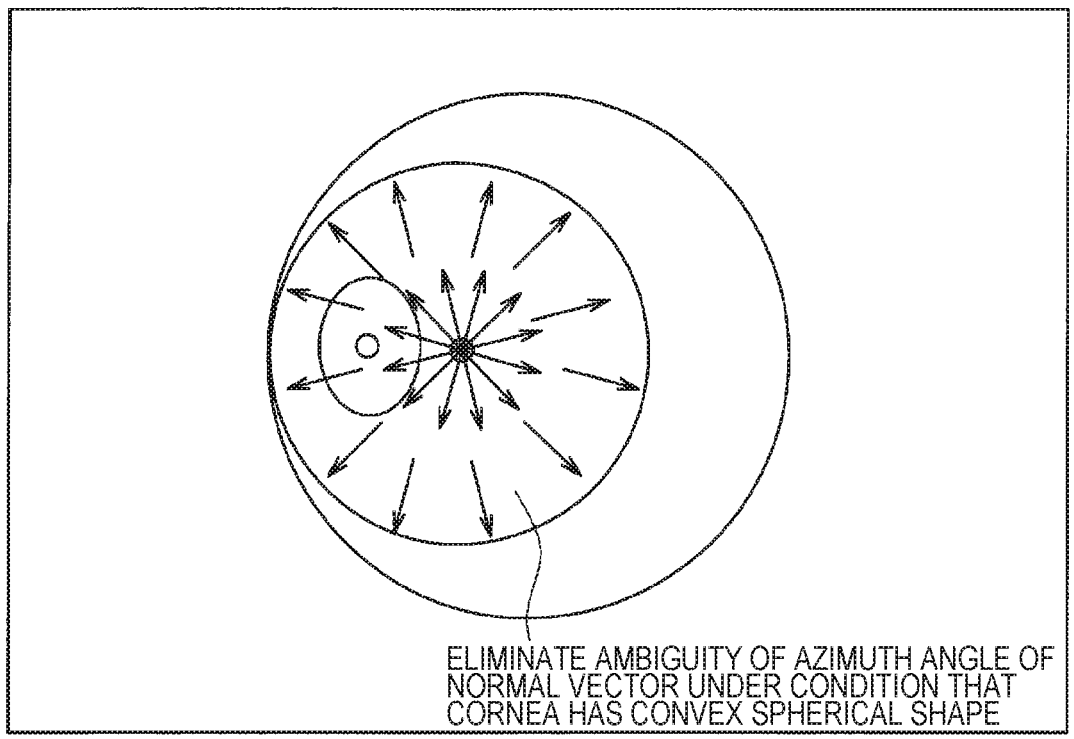
FIG. 7 is an illustration that explains an example of the processes of the information processing method according to the present embodiment.

FIG. 7 is an illustration that explains an example of the processes of the information processing method according to the present embodiment, showing an example of the normal vectors after eliminating the ambiguity of the azimuth angle.

The information processing apparatus according to the present embodiment estimates the center position of the cornea (S112). The center position of the cornea is represented, for example, by a three-dimensional coordinate.

The information processing apparatus according to the present embodiment obtains the center position of the cornea, for example, by performing any of the following processes in a first example shown in (1) to a fourth example shown in (4), thereby estimating the center position of the cornea.

(1) A First Example of the Process for Estimating the Center Position of the Cornea: The First Example of the Estimation on the Basis of a Plurality of the Normal Lines on the Cornea.

The information processing apparatus according to the present embodiment estimates the center position of the cornea, for example, on the basis of a plurality of the normal lines on the cornea.

The information processing apparatus according to the present embodiment, for example, obtains the nearest neighbor point of the plurality of the normal lines on the cornea and set the nearest neighbor point thus obtained as the center position of the cornea. The information processing apparatus according to the present embodiment obtains the nearest neighbor point of the plurality of the normal lines on the cornea, for example, on the basis of a radius of the cornea.

The radius of the cornea used for estimating the center position of the cornea by the information processing apparatus according to the present embodiment may be a preset fixed value or a variable value obtained by adjusting the fixed value with an adjusting value corresponding to the detection object. In the case where the radius of the cornea is the variable value, the information processing apparatus according to the present embodiment specifies the adjusting value corresponding to the detection object, for example, on the basis of a "recognition result of the detection object specified by any methods such as biometric authentication and password authentication" and a "table (or database, the same hereinafter) in which the detection object and the adjusting value are associated with each other.

(2) A Second Example of the Process for Estimating the Center Position of the Cornea: The Second Example of the Estimation on the Basis of the Plurality of the Normal Lines on the Cornea.

The information processing apparatus according to the present embodiment estimates the center position of the cornea, for example, on the basis of the plurality of the normal lines on the cornea.

Figure 8:
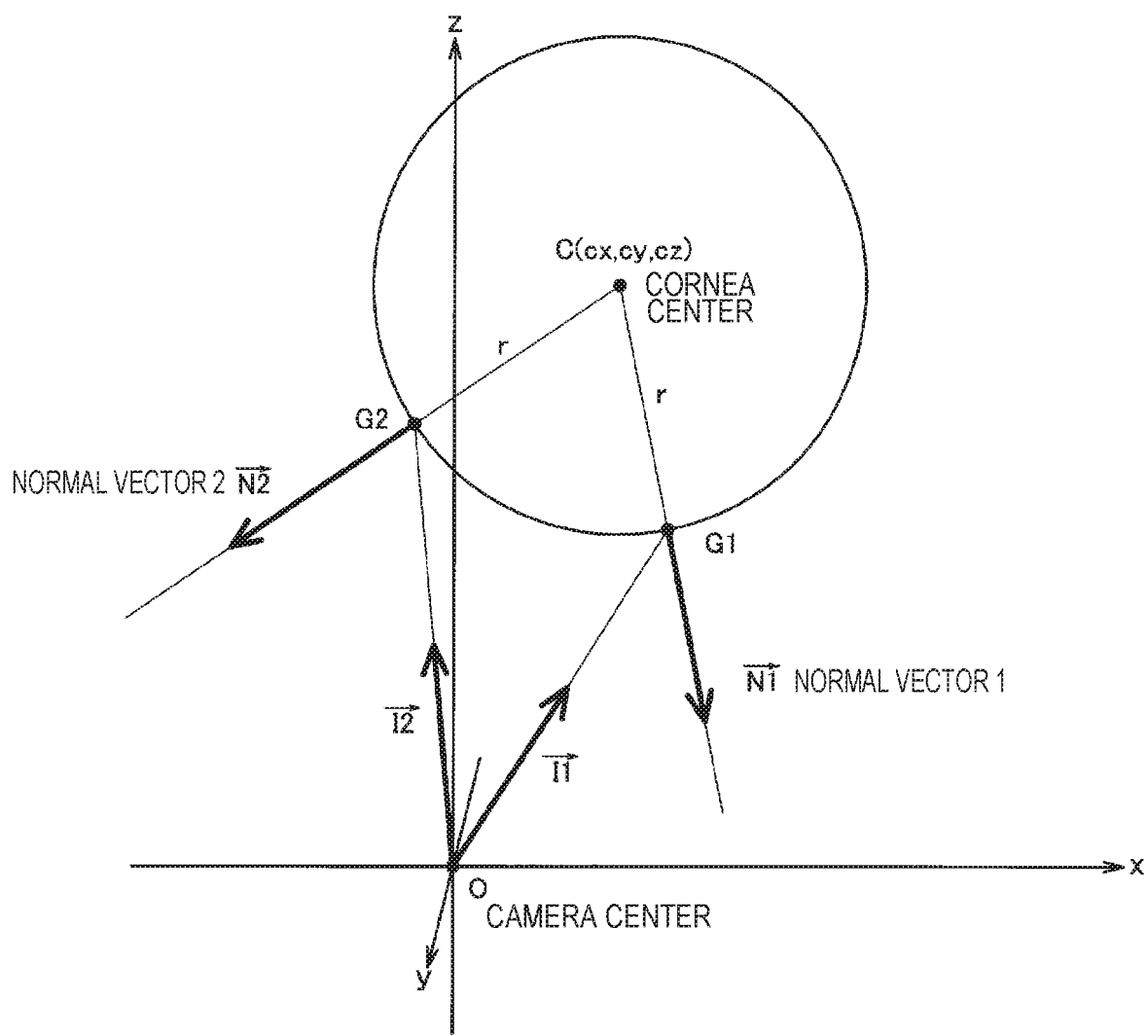
FIG. 8 is an illustration that explains an example of the processes of the information processing method according to the present embodiment.

FIG. 8 is an illustration that explains an example of the processes of the information processing method according to the present embodiment. FIG. 8 shows an example in which the center position of the cornea is estimated on the basis of two normal lines on the cornea.

A center position of the imaging device (hereinafter, also referred to as a "camera center") is used for setting the origin O of the coordinate system, and the center position of the cornea is represented by C=(cx. cy, cz), the radius of the cornea is represented by r, and points on the cornea are represented by G1 and G2. Further, a normal vector on the point G1 on the cornea is represented by N1, a normal vector on the point G2 on the cornea by N2, a vector extending from the center position O of the imaging device to the point G1 on the cornea by I1, a vector extending from the center position O of the imaging device to the point G2 on the cornea by I2, a distance between the center position O of the imaging device and the point G1 on the cornea by d1, a distance between the center position O of the imaging device and the point G2 on the cornea by d2. In the following description, the distance d1 between the center position O of the imaging device and the point G1 on the cornea is also referred to as a "distance d1" and the distance d2 between the center position O of the imaging device and the point G2 on the cornea is also referred to as a "distance d2".

In this coordinate system, the coordinates of the center position C of the cornea, the distance d1 between the center position O of the imaging device and the point G1 on the cornea, and the distance d2 between the center position O of the imaging device and the point G2 on the cornea are unknown. In the following description, the distance d1 between the center position O of the imaging device and the point G1 on the cornea is also referred to as a "distance d1" and the distance d2 between the center position O of the imaging device and the point G2 on the cornea is also referred to as a "distance d2".

The information processing apparatus according to the present embodiment obtains the coordinates of the center position C of the cornea, for example, by solving an equation 1 below for the distance d1 and the distance d2 under the condition that the coordinates of the center position C of the cornea, the distance d1, and the distance d2 are unknown. Each vector indicated in the Equation 1 described herein includes an x-coordinate component, a y-coordinate component, and a z-coordinate component, thus the Equation 1 is considered as a non-linear simultaneous equation. Further, a vector extending from the center position O of the imaging device to the center position C of the cornea is represented by an Equation 2 below, and the distance d1 and the distance d2 are represented by an Equation 3 below.

[Math. 1]
$$d1 \cdot \vec{I1} - r \cdot \vec{N1} = d2 \cdot \vec{I2} - r \cdot \vec{N2} \quad \text{(Equation 1)}$$

[Math. 2]
$$\begin{cases} \vec{OC} = \vec{OG1} + \vec{G1C} \\ \vec{OC} = \vec{OG2} + \vec{G2C} \end{cases} \quad \text{(Equation 2)}$$

[Math. 3]
$$\begin{cases} d1 = |\vec{OG1}| \\ d2 = |\vec{OG2}| \end{cases} \quad \text{(Equation 3)}$$

The information processing apparatus according to the present embodiment obtains the position of the point G1 on the cornea and the position of the point G2 on the cornea using the distance d1 and the distance d2 obtained by the above Equation 1, and the above Equation 3. Then, the information processing apparatus according to the present embodiment obtains the coordinates of the center position C of the cornea using the position of the point G1 on the cornea, the normal vector N1 on the point G1 on the cornea, the position of the point G2 on the cornea, the normal vector N2 on the point G2 on the cornea, and the radius r of the cornea.

The information processing apparatus according to the present embodiment can estimate the center position of the cornea, for example, on the basis of the two normal lines on the cornea as described above.

Note that, in a case where there are N number (N is an integer equal to or more than 3) of the normal lines on the cornea, the information processing apparatus according to the present embodiment can obtain the coordinates of the center position C of the cornea, for example, by extending the above Equation 1 to N number of the normal lines and obtaining N number of unknown values, similarly to the case where the calculation is based on the two normal lines on the cornea. Note that increasing the number of the normal lines on the cornea used for estimating the coordinates of the center position C of the cornea can reduce an effect of noise or the like.

(3) A Third Example of the Process for Estimating the Center Position of the Cornea: The Third Example of the Estimation on the Basis of the Plurality of the Normal Lines on the Cornea.

Note that the example of the estimation on the basis of the plurality of the normal lines on the cornea is not limited to the process in the first example above and the process of the second example above.

As described above, the information processing apparatus according to the present embodiment can also estimate the center position of the cornea in the eye of the detection object on the basis of the normal lines obtained from the first polarization image and the second polarization image constituting the stereo image.

In the case where the center position of the cornea in the eye of the detection object is estimated on the basis of the first polarization image and the second polarization image, the information processing apparatus according to the present embodiment obtains parallax on the basis of the first polarization image and the second polarization image. Then, the information processing apparatus according to the present embodiment estimates the center position of the cornea using the parallax thus obtained.

Figure 9:
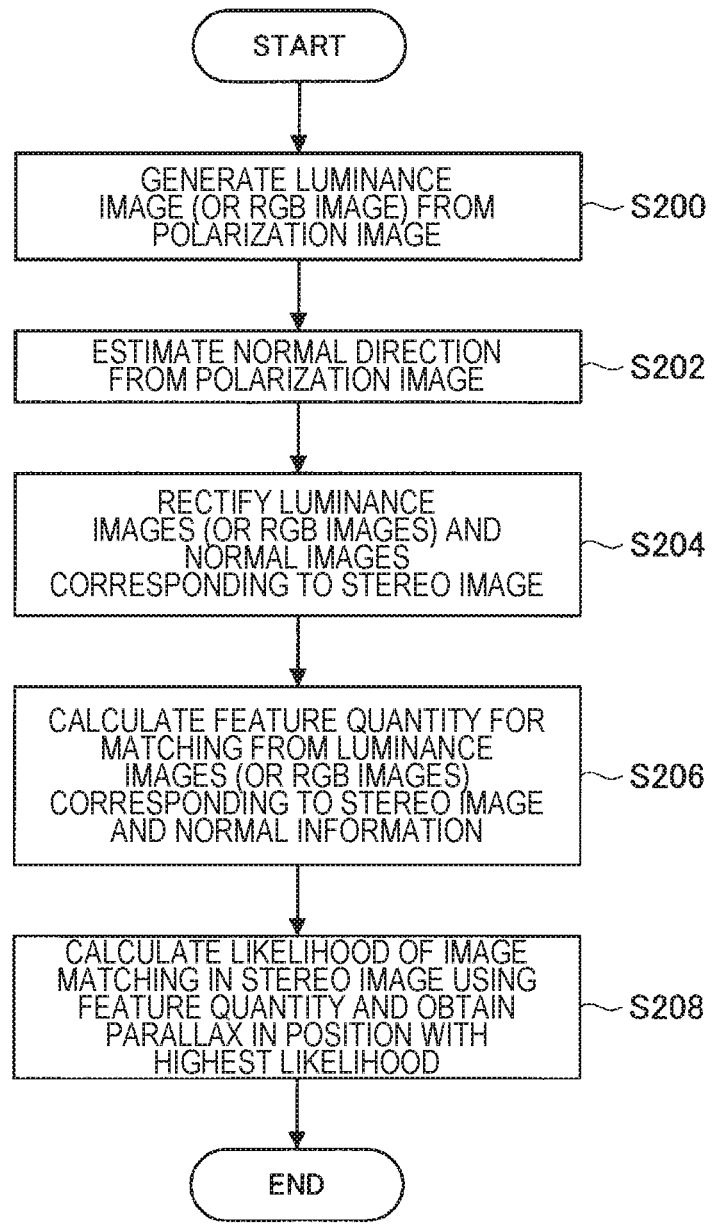
FIG. 9 is a flowchart that explains an example of the processes of the information processing method according to the present embodiment

(3-1) An Example of the Processes for Obtaining the Parallax on the Basis of the First Polarization Image and the Second Polarization Image A description will be given for an example of the processes for obtaining the parallax on the basis of the first polarization image and the second polarization image. FIG. 9 is a flowchart that explains an example of the processes of the information processing method according to the present embodiment, showing an example of the processes for obtaining the parallax on the basis of the first polarization image and the second polarization image.

The information processing apparatus according to the present embodiment generates the luminance image from the first polarization image and generates the luminance image from the second polarization image (S200) as in the step S100 in FIG. 5. Hereinafter, the luminance image generated from the first polarization image is referred to as a "first luminance image" and the luminance image generated from the second polarization image is referred to as a "second luminance image".

Note that the information processing apparatus according to the present embodiment can also use the luminance image corresponding to the first polarization image and the luminance image corresponding to the second polarization image, both being generated by the process in the step S100 in FIG. 5, in the processes in and after a step S202 without performing the process in the step S200.

The information processing apparatus according to the present embodiment estimates a normal direction in each of the first polarization image and the second polarization image (S202). The information processing apparatus according to the present embodiment estimates the normal direction in each of the first polarization image and the second polarization image, for example, by performing the process similar to that in the step S106 in FIG. 5. Hereinafter, the normal image generated from the first polarization image is referred to as a "first normal image" and the normal image generated from the second polarization image is referred to as a "second normal image".

Note that the information processing apparatus according to the present embodiment can also use the result of the process in the step S106 in FIG. 5 in the processes in and after a step S204 without performing the process in the step S202.

The information processing apparatus according to the present embodiment performs rectification on the luminance images corresponding to the stereo image (the first polarization image and the second polarization image, the same hereinafter) and the normal images corresponding to the stereo image (S204). The information processing apparatus according to the present embodiment performs rectification on the luminance images corresponding to the stereo image, for example, by warping the first luminance image and the second luminance image such that the normal lines of the corresponding pixels match each other. Further, the information processing apparatus according to the present embodiment performs rectification on the normal images corresponding to the stereo image, for example, by warping the first normal image and the second normal image such that the normal lines of the corresponding pixels match each other. An example of the warping will be described below.

The information processing apparatus according to the present embodiment calculates a feature quantity for matching the first luminance image and the second luminance image (hereinafter, referred to as a "feature quantity for matching") on the basis of the luminance images corresponding to the stereo image and normal information indicating the normal lines obtained from the normal images corresponding to the stereo image (S206). The feature quantity for matching is calculated, for example, for a plurality of the corresponding pixels in the stereo image.

Examples of a method of obtaining the feature quantity for matching described herein include "absolute difference (AD)", "sum of absolute differences (SAD)", "normalized cross correlation (NCC)", "census transform", "local binary pattern (LBP)", and the like.

However, a known method of obtaining the feature quantity for matching such as "AD" performs a matching process mainly using texture as a feature. Thus, for example, in a case where an imaging object having little texture is imaged with the stereo camera, it may be difficult to perform matching between the first luminance image and the second luminance image by solely using the known method of obtaining the feature quantity for matching.

In contrast, the information processing apparatus according to the present embodiment calculates the feature quantity for matching, for example, on the basis of a score obtained using the normal information. Further, as described below, the information processing apparatus according to the present embodiment can also calculate the feature quantity for matching on the basis of one or more scores obtained using one or more known methods of obtaining the feature quantity for matching described above.

Calculating the feature quantity for matching on the basis of the score obtained using the normal information can improve accuracy of the matching even if the imaging object having little texture is imaged. Thus, accuracy of the matching can be improved by calculating the feature quantity for matching on the basis of the score obtained using the normal information as compared to the case where the known method of obtaining the feature quantity for matching described above is solely used.

The information processing apparatus according to the present embodiment calculates the feature quantity for matching, for example, by an Equation 4 below.

Note that "Matching Score" in the Equation 4 corresponds to the feature quantity for matching. Further, "ScoreA" in the Equation 4 represents a score obtained by one known method of obtaining the feature quantity for matching and "a" in the Equation 4 represents a coefficient defining a weight for "ScoreA". "ScoreB" in the Equation 4 represents a score obtained by another known method of obtaining the feature quantity for matching and "b" in the Equation 4 represents a coefficient defining a weight for "ScoreB". Further, "ScoreC" in the Equation 4 represents a score obtained by using the normal information and "c" in the Equation 4 represents a coefficient defining a weight for "ScoreC".

Note that each of the coefficients "a", "b", and "c" indicated in the Equation 4 may be a preset fixed value or a variable value which can be changed by an operation of a user of the information processing apparatus according to the present embodiment or the like. Further, either or both of the coefficient "a" and the coefficient "b" may be zero (0).

$$\text{Matching Score} = a \cdot \text{Score}A + b \cdot \text{Score}B + c \cdot \text{Score}C \quad \text{(Equation 4)}$$

Note that the Equation for calculating the feature quantity for matching is not limited to the above Equation 4. For example, the information processing apparatus according to the present embodiment can also calculate the feature quantity for matching by using scores obtained by 3 or more known methods of obtaining the feature quantity for matching.

Below is an example of a score calculation method using the known methods of obtaining the feature quantity for matching, in which ScoreA is a score obtained by the "census transform" and ScoreB is a score obtained by the "AD". Further, an example of the score calculation method using the normal information is described.

FIGS. 10A, 10B, 10C, 10D, and 10E are illustrations that explains an example of the calculation method of the feature quantity for matching according to the present embodiment, showing an example of the score calculation method using the "census transform". FIG. 10A shows the luminance image corresponding to the left eye (the first luminance image or the second luminance image) and FIG. 10B shows the luminance image corresponding to the right eye (the second luminance image or the first luminance image).

In the "census transform", a patch having an attention pixel as a center is set in the luminance image corresponding to the left eye and the luminance image corresponding to the right eye, and magnitude relations between the attention pixel and other pixels in the patch are represented by 1 or 0. Then, in the "census transform", a result of the magnitude relations between the attention pixel and other pixels is converted to a bit pattern to determine the feature quantity.

For example, in a case where the patch is constituted by 5×5 pixels having the attention pixel as a center as shown in FIG. 10C, the magnitude relations between the attention pixel and other pixels in the luminance image corresponding to the left eye are represented as shown in FIG. 10D and converted to a bit pattern as shown in FIG. 10E. In the case where the patch is constituted by 5×5 pixels as shown in FIGS. 10A, 10B, 10C, 10D, and 10E, the feature quantity of 24 [bit] is generated.

Further, although not shown in FIGS. 10A, 10B, 10C, 10D, and 10E, the feature quantity is obtained in the similar manner for the attention pixel in the luminance image corresponding to the right eye. The attention pixel in the luminance image corresponding to the right eye described herein is specified, for example, by searching, in the luminance image corresponding to the right eye, a pixel that is present on the same line as the attention pixel in the luminance image corresponding to the left eye serving as a reference.

Then, in the "census transform", a hamming distance between the feature quantity of the attention pixel on the basis of the luminance image corresponding to the left eye and the feature quantity of the attention pixel on the basis of the luminance image corresponding to the right eye is calculated and the hamming distance thus calculated is determined as a score.

Note that, in a case where the luminance images corresponding to the stereo image are rectified as shown in the step S204 in FIG. 9, the feature quantity and the score of the patch having the attention pixel as a center are calculated after the warping is performed such that the normal directions of the luminance images corresponding to the stereo image match each other.

FIGS. 11A, 11B, and 11C are illustrations that explains an example of the calculation method of the feature quantity for matching according to the present embodiment, showing an example of performing the warping using one normal line. FIG. 11A shows the luminance image corresponding to the left eye (the first luminance image or the second luminance image) and FIG. 10B shows the luminance image corresponding to the right eye (the second luminance image or the first luminance image). Further, FIG. 11C shows the luminance image corresponding to the right eye after being subjected to the warping.

Calculating the score using the "census transform" on the basis of the luminance image corresponding to the left eye and the luminance image corresponding to the right eye after being subjected to the warping as shown in FIG. 11C makes it possible to calculate the feature quantity for matching capable of obtaining the parallax with higher accuracy.

Note that, although FIGS. 11A, 11B and 11C show the example in which the warping is performed using one normal line, it is also possible to perform the warping twice using two normal lines in consideration of the ambiguity of the azimuth angle described above, calculate the feature quantity and the score on each normal line, and then adopt smaller values (or larger values).

FIGS. 12A and 12B are illustrations that explains an example of the calculation method of the feature quantity for matching according to the present embodiment, showing an example of the score calculation method using the "AD". FIG. 12A shows the luminance image corresponding to the left eye (the first luminance image or the second luminance image) and FIG. 12B shows the luminance image corresponding to the right eye (the second luminance image or the first luminance image).

In the "AD", a pixel value of each attention pixel of the luminance images corresponding to the stereo image is determined as the feature quantity. Then, in the "AD", an absolute value of a difference between the pixel values of the attention pixels is determined as the score.

FIGS. 13A and 13B are illustrations that explains an example of the calculation method of the feature quantity for matching according to the present embodiment, showing an example of the score calculation method using the normal information. FIG. 13A shows the luminance image corresponding to the left eye (the first luminance image or the second luminance image) and FIG. 13B shows the luminance image corresponding to the right eye (the second luminance image or the first luminance image).

In a case of searching the attention pixel in the luminance image corresponding to the right eye using the attention pixel in the luminance image corresponding to the left eye as a reference, an "inner product of the normal line of the attention pixel in the luminance image corresponding to the left eye (L_Normal_1) and the normal line of the attention pixel in the luminance image corresponding to the right eye (R_Normal_1)" and an "inner product of the normal line of the attention pixel in the luminance image corresponding to the left eye (L_Normal_1) and the normal line of the attention pixel in the luminance image corresponding to the right eye (R_Normal_2)" are each calculated. Then, a larger value of the inner products thus calculated is adopted as the score.

The attention pixel used in the calculation has two normal lines due to the ambiguity in the azimuth angle as described above. Note that there are four (2×2) combinations of the normal lines for calculating their inner products, thus it is possible to calculate the inner products corresponding to the four combinations. However, the score with sufficient accuracy can be obtained even if one of the normal lines is fixed in one image and the inner products are calculated in two combinations using the fixed normal line and two normal lines in the other image as described above.

The information processing apparatus according to the present embodiment calculates the feature quantity for matching, for example, by performing an arithmetic operation represented by the above Equation 4 in the step S206 in FIG. 9.

Again, referring to FIG. 9, an example of the processes for obtaining the parallax on the basis of the first polarization image and the second polarization image will be described. The information processing apparatus according to the present embodiment calculates likelihood of image matching in the stereo image on the basis of the feature quantity for matching calculated in the step S206 and obtain the parallax in a position of the pixel with the highest likelihood in the stereo image (S208).

The information processing apparatus according to the present embodiment obtains the parallax on the basis of the first polarization image and the second polarization image, for example, by performing the processes shown in FIG. 9. Note that, needless to say, the example of the processes for obtaining the parallax on the basis of the first polarization image and the second polarization image is not limited to the one shown in FIG. 9.

(3-2) Processes for Estimating the Center Position of the Cornea Using the Parallax The information processing apparatus according to the present embodiment estimates the center position of the cornea using the obtained parallax.

Figure 14:
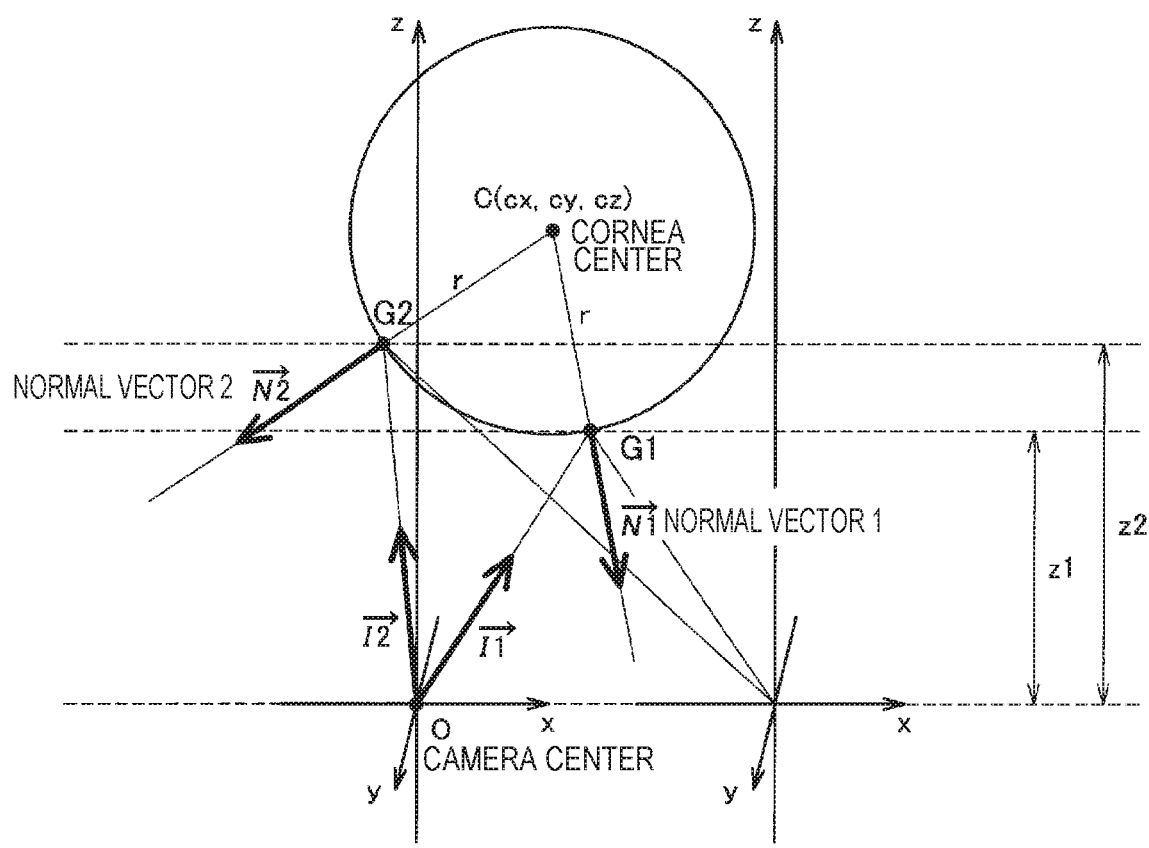
FIG. 14 is an illustration that explains an example of the processes of the information processing method according to the present embodiment.

FIG. 14 is an illustration that explains an example of the processes of the information processing method according to the present embodiment. FIG. 14 shows an example of estimating the center position of the cornea on the basis of two normal lines on the cornea and the parallax.

The center position of one imaging device constituting the stereo camera (the camera center) is used for setting the origin O of the coordinate system, and the center position of the cornea is represented by C=(cx. cy, cz), the radius of the cornea is represented by r, and the points on the cornea are represented by G1 and G2. Further, the normal vector on the point G1 on the cornea is represented by N1, the normal vector on the point G2 on the cornea by N2, the vector extending from the center position O of the one imaging device to the point G1 on the cornea by I1, the vector extending from the center position O of the one imaging device to the point G2 on the cornea by I2, the distance between the center position O of the one imaging device and the point G1 on the cornea by d1, the distance between the center position O of the one imaging device and the point G2 on the cornea by d2. In the following description, the distance d1 between the center position O of the one imaging device and the point G1 on the cornea is also referred to as the "distance d1" and the distance d2 between the center position O of the one imaging device and the point G2 on the cornea is also referred to as the "distance d2".

The parallax obtained by the processes in the above (3-1) determines "z1" corresponding to a z coordinate of the point G1 on the cornea and "z2" corresponding to a z coordinate of the point G2 on the cornea. The information processing apparatus according to the present embodiment calculates the distance d1 and distance d2 by performing an arithmetic operation represented by an Equation 5 below. In the Equation 5 described herein, "$f_x$" represents a focal length, one of intrinsic parameters of the imaging device, in an x direction and "$f_y$" represents a focal length in a y direction. Further, in the Equation 5, (u1, v1) represents the coordinates of the point G1 on the cornea on the image and (u2, v2) represents the coordinates of the point G2 on the cornea on the image. In the Equation 5, "u1", "v1", "u2", and "v2" are represented, for example, by a unit [pix].

[Math. 4]

$$\begin{cases} d1 = \sqrt{x1^2 + y1^2 + z1^2} \\ d2 = \sqrt{x2^2 + y2^2 + z2^2} \\ x1 = \frac{z1}{f_x} \cdot u1 \\ y1 = \frac{z1}{f_y} \cdot v1 \\ x2 = \frac{z2}{f_x} \cdot u2 \\ y2 = \frac{z2}{f_y} \cdot v2 \end{cases} \quad \text{(Equation 5)}$$

Once the distance d1 and the distance d2 are calculated, the information processing apparatus according to the present embodiment obtains the radius r of the cornea from the Equation 1 above, thereby obtaining the coordinates of the center position C of the cornea.

As described above, the position of the point G1 on the cornea and the position of the point G2 on the cornea are determined by the obtained distance d1 and distance d2, and the Equation 3 above. The information processing apparatus according to the present embodiment obtains the coordinates of the center position C of the cornea using the position of the point G1 on the cornea, the normal vector N1 on the point G1 on the cornea, the position of the point G2 on the cornea, the normal vector N2 on the point G2 on the cornea, and the radius r of the cornea obtained by the Equation 1 above.

The information processing apparatus according to the present embodiment can estimate the center position of the cornea by using the parallax, for example, as described above.

Note that, in a case where there are N number (N is an integer equal to or more than 3) of the normal lines on the cornea, the information processing apparatus according to the present embodiment can obtain the coordinates of the center position C of the cornea, for example, by extending the Equation 1 above to N number of the normal lines and performing calculation similarly to the case where the Equation 1 is based on two normal lines on the cornea.

(4) A Fourth Example of the Process for Estimating the Center Position of the Cornea: An Estimation Using Random Sample Consensus (RANSAC).

The information processing apparatus according to the present embodiment estimates the center position of the cornea, for example, by solving an optimization problem using RANSAC.

The information processing apparatus according to the present embodiment, for example, obtains central coordinates of the cornea by using M number (at least 2) of the normal vectors and re-projects a sphere of a radius r centering on the obtained central coordinates of the cornea onto the image. Further, the information processing apparatus according to the present embodiment calculates the inner product of the normal line on the sphere and the normal line obtained from the polarization image and counts the number of the normal lines that exceed a set threshold. Then, the information processing apparatus according to the present embodiment obtains the central coordinates of the sphere by optimization using the normal lines of the largest number, thereby estimating the center position of the cornea.

Figure 15:
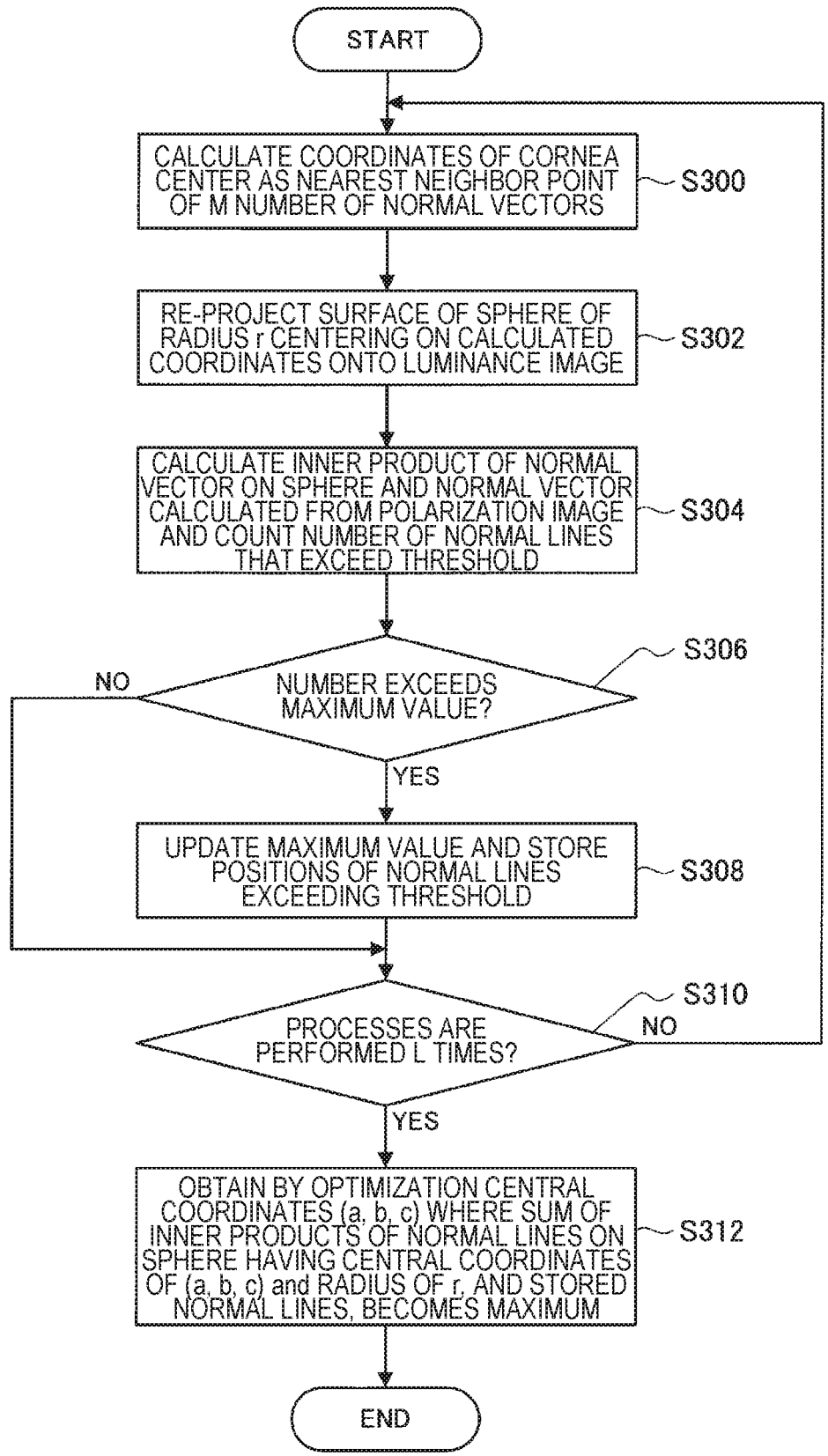
FIG. 15 is a flowchart that explains an example of the processes of the information processing method according to the present embodiment.

FIG. 15 is a flowchart that explains an example of the processes of the information processing method according to the present embodiment, showing an example of the processes for estimating the center position of the cornea using the RANSAC.

The information processing apparatus according to the present embodiment calculates the coordinates of the center position of the cornea, for example, as the nearest neighbor point of M number of the normal vectors, similarly to the process in the first example described in the above (1) (S300).

The information processing apparatus according to the present embodiment re-projects a surface of the sphere of the radius r centering on the coordinates calculated in the step S300 onto the luminance image on the basis of the polarization image (S302). The radius r described herein corresponds to the radius of the cornea. The radius r may be a preset fixed value or a variable value obtained by adjusting the fixed value with an adjusting value corresponding to the detection object.

The information processing apparatus according to the present embodiment calculates the inner product of the normal line on the sphere and the normal line obtained from the polarization image and counts the number of the normal lines that exceed the set threshold (S304). The above-mentioned threshold may be a preset fixed value or a variable value which can be changed by an operation of the user of the information processing apparatus according to the present embodiment or the like.

The information processing apparatus according to the present embodiment determines whether the number of the normal lines counted in the step S304 exceeds the maximum value (S306). As an initial value of the maximum value described herein, a set value such as zero (0) may be used. The information processing apparatus according to the present embodiment determines that the number of the counted normal lines exceeds the set maximum value, for example, if the number of the normal lines described above is larger than the maximum value described above, or the number of the normal lines described above is equal to or larger than the maximum value described above.

If it is not determined that the maximum value is exceeded in the step S306, the information processing apparatus according to the present embodiment performs the processes from a step S310 described below.

Further, if it is determined that the maximum value is exceeded in the step S306, the information processing apparatus according to the present embodiment updates the maximum value to the number of the counted normal lines and stores positions of the normal lines exceeding the set threshold in a recording medium such as a random access memory (RAM) (S308).

If it is not determined that the maximum value is exceeded in the step S306, or the process in the step 308 is performed, the information processing apparatus according to the present embodiment determines whether the processes are performed L times (L is a set integer) (S310). A value of L may be a preset fixed value or a variable value which can be changed by an operation of the user of the information processing apparatus according to the present embodiment or the like.

If it is not determined that the processes are performed L times in the step S310, the information processing apparatus according to the present embodiment repeats the processes from the step S300.

Further, if it is determined that the processes are performed L times in the step S310, the information processing apparatus according to the present embodiment obtains by optimization, for example, the central coordinates of the cornea where the "sum of the inner products of the normal lines of the sphere of the radius r centering on the central coordinates of the cornea, the sphere being subjected to re-projection in the step S302, and the normal lines stored in the recording medium in the step S308" becomes the maximum (S312).

The information processing apparatus according to the present embodiment estimates the center position of the cornea, for example, by performing the processes shown in FIG. 15. Note that, needless to say, the processes for estimating the center position of the cornea using the RANSAC is not limited to the example shown in FIG. 15.

The information processing apparatus according to the present embodiment estimates the center position of the cornea in the step S112 in FIG. 5, for example, by performing any of the processes in the first example described in the above (1) to the fourth example described in the above (4).

Again, referring to FIG. 5, an example of the processes of the information processing method according to the present embodiment will be described. The information processing apparatus according to the present embodiment estimates a center position of the pupil in the eye on the basis of the estimated center position of the cornea and the radius of the cornea (S114). The information processing apparatus according to the present embodiment estimates the center position of the pupil, for example, by using a set distance between the pupils in the corneas and taking refraction or the like into consideration, similarly to the case of using the corneal reflection method.

The information processing apparatus according to the present embodiment obtains an optical axis vector indicating an optical axis corresponding to the gaze of the detection object on the basis of the center position of the cornea estimated in the step S112 and the center position of the pupil estimated in the step S114 (S116). The optical axis described herein is the normal line of the cornea passing through the center position of the pupil and corresponds to, for example, a line connecting the center position of the cornea and the center position of the pupil. The information processing apparatus according to the present embodiment obtains the optical axis vector, for example, similarly to the case of using the corneal reflection method.

The information processing apparatus according to the present embodiment obtains a gaze vector indicating a visual axis of the detection object on the basis of the optical axis vector obtained in the step S116 and calibration information (S118).

The visual axis is a line connecting the nodal point (a central back surface of the lens) and the fovea and corresponds to an axis of actual sight of the detection object. That is, the gaze of the detection object can be detected by obtaining the gaze vector.

In general, the visual axis does not coincide with the optical axis and the visual axis is inclined by about 4[°] to 8[°] with respect to the optical axis. Further, the inclination of the visual axis with respect to the optical axis differs from person to person.

In order to reduce a deviation of the visual axis from the optical axis described above, a correction of the optical axis vector (hereinafter referred to as "calibration") is performed on the basis of the calibration information. The calibration is performed, for example, for each eye of the detection object.

The calibration information described herein is data for performing the calibration. The calibration information includes data indicating the deviation of the visual axis from the optical axis (hereinafter, referred to as an "offset"). The offset is obtained, for example, as follows.

A difference between the optical axis vector obtained from the detection object who views a calibration position and a vector connecting a reference position corresponding to the eyeball and the calibration position is obtained as the offset.

The information processing apparatus according to the present embodiment detects the gaze of the detection object on the basis of the normal line obtained from the polarization image, for example, by performing the processes shown in FIG. 5 as the detection processes of the information processing method according to the present embodiment. Note that, needless to say, the example of the detection processes of the information processing method according to the present embodiment are not limited to the one shown in FIG. 5.

[3] An Example of Effects Achieved by Using the Information Processing Method According to the Present Embodiment Performing the detection processes of the information processing method according to the present embodiment can achieve, for example, the following effects. Note that, needless to say, the effects achieved by performing the detection processes of the information processing method according to the present embodiment are not limited to the following examples.

Using the polarization imaging allows the detection of the gaze of the detection object only by imaging with the imaging device without using a light source such as the LED.

Not using a light source such as the LED circumvents degradation of gaze accuracy caused by an outlier of the Purkinje image, or the like, occurring when the corneal reflection method is used to detect the gaze.

Obtaining the plurality of the normal vectors on the basis of the polarization image can improve estimation accuracy of the center position of the cornea.

[4] Other Examples of the Processes of the Information Processing Method According to the Present Embodiment Note that the processes of the information processing method according to the present embodiment are not limited to the "detection processes for detecting the gaze of the detection object on the basis of the normal line obtained from the polarization image".

For example, the information processing apparatus according to the present embodiment can perform "processes for detecting various objects other than the gaze (hereinafter referred to as "other detection processes") on the basis of the normal line obtained from the polarization image". Examples of an application example of the other detection processes according to the present embodiment include a first example described in (I) to a fourth example described in (IV) below.

(I) A First Example of the Other Detection Processes

The information processing apparatus according to the present embodiment, for example, detects the center position of the cornea in the eye of the detection object on the basis of the normal line obtained from the polarization image. The information processing apparatus according to the present embodiment detects the center position of the cornea, for example, by performing the processes in the steps S100 to S112 in FIG. 5.

(II) A Second Example of the Other Detection Processes

The information processing apparatus according to the present embodiment, for example, detects one or both of posture of an object indicated by information indicating a shape and a change in the posture of the object on the basis of the normal line obtained from the polarization image and the information indicating a shape of the object.

The information processing apparatus according to the present embodiment detects the posture of the object, for example, by estimating the posture of the object indicated by the information indicating a shape through a combination of the normal line obtained from the polarization image. Further, the formation processing device according to the present embodiment detects the change in the posture of the object, for example, by estimating the change in the posture of the object indicated by the information indicating a shape through a comparison of the combinations of the normal lines obtained from a plurality of the polarization images obtained by imaging at different time points.

Examples of the application example of the other detection processes of the second example include an "example of detecting the posture of the eye on the basis of the polarization image in which the eye of a person or the like is imaged and the information indicating a shape of the eyeball (an example of the object)", an "example of detecting the posture of a controller of a game machine on the basis of the polarization image in which the controller is imaged and the information indicating a shape of the controller (an example of the object)", and the like.

Further, the information processing apparatus according to the present embodiment can also detect a space position (a three-dimensional position) of an object on the basis of a distance of the object indicated by the information indicating a shape and the imaging device. The distance of the object and the imaging device described above is detected, for example, by a distance sensor that detects a distance using any system such as a time-of-flight (TOF) system, or the like.

(III) A Third Example of the Other Detection Processes

The information processing apparatus according to the present embodiment, for example, detects an object facing to a certain direction with respect to the imaging device among the objects (the imaging objects) imaged with the imaging device on the basis of the normal line obtained from the polarization image.

The information processing apparatus according to the present embodiment, for example, specifies a region in which the normal vector obtained from the polarization image is within a range of a set angle in the luminance image (or the RGB image) on the basis of the polarization image. Then, the information processing apparatus according to the present embodiment detects the object facing to a certain direction with respect to the imaging device by subjecting the specified region to an object recognition process using any object recognition technique.

Examples of the application examples of the other detection processes of the third example include an example of detecting a freely-selected object, such as a road sign and a signboard, on the basis of the polarization image imaged with the imaging device mounted in a mobile object such as an automobile, and the like.

Performing the other detection processes of the third example can limit a region that is subjected to the object recognition process. Thus, performing the other detection processes of the third example can, for example, reduce processing load of the object recognition process.

(IV) A Fourth Example of the Other Detection Processes

The information processing apparatus according to the present embodiment, for example, detects an object indicated by information indicating combinations of the normal lines from the polarization image on the basis of the normal line obtained from the polarization image and the information indicating combinations of the normal lines of the object.

The information processing apparatus according to the present embodiment, for example, performs matching between combinations of the normal lines obtained from the polarization image and combinations of the normal lines indicated by the information indicating combinations of the normal lines. Then, the processing device according to the present embodiment detects the object indicated by the information indicating combinations of the normal lines from the polarization image, for example, by detecting a region in which both combinations of the normal lines match each other in the polarization image (or the luminance image (or the RGB image) on the basis of the polarization image).

As one application example of the other detection processes of the fourth, for example, an "example of determining an imitation by using a fact that objects made from different raw materials have different combinations of the normal lines due to differences in diffuse reflection and specular reflection" can be mentioned. In the one application example described above, whether the object is the imitation or not is determined by imaging the object with the imaging device using the polarization imaging technique, thus determining the imitation becomes easier.

Further, as another application example of the other detection processes of the fourth example, for example, an "example of detecting a region that includes a specified imaging object in the polarization image after a plurality of imaging objects are imaged with the imaging device" can be mentioned. In the another application example described above, for example, the processing load of the object recognition process can be reduced, similarly to the other detection processes of the third example described above.

(The Information Processing Apparatus According to the Present Embodiment)

Next, a description will be given for an example of a configuration of the information processing apparatus according to the present embodiment capable of performing the processes of the information processing method according to the present embodiment described above.

Figure 16:
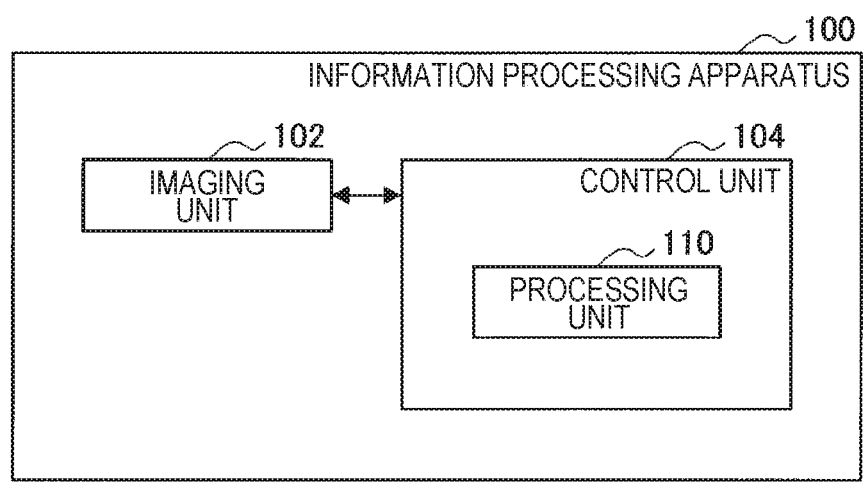
FIG. 16 is a block diagram that shows an example of a configuration of an information processing apparatus according to the present embodiment.

FIG. 16 is a block diagram that shows an example of a configuration of an information processing apparatus 100 according to the present embodiment. The information processing apparatus 100 includes, for example, an imaging unit 102 and a control unit 104.

Further, the information processing apparatus 100 may include, for example, a read-only memory (ROM, not illustrated), a RAM (not illustrated), a storage unit (not illustrated), a communication unit (not illustrated) that performs wireless or wired communication with an external apparatus, an operation unit (not illustrated) that can be operated by a user, a display unit (not illustrated) that displays various images on a display screen, and the like. The information processing apparatus 100 connects the above-mentioned constituent elements, for example, by a bus serving as a data transmission path. The information processing apparatus 100 connects the above-mentioned constituent elements, for example, by a bus serving as a data transmission path. The information processing apparatus 100 is driven, for example, by the power supplied from an internal power source such as a battery provided in the information processing apparatus 100, the power supplied from a connected external power source, or the like.

The ROM (not illustrated) stores a program used by the control unit 104 and control data such as an arithmetic parameter. The RAM (not illustrated) temporarily stores a program executed by the control unit 104 and the like.

The storage unit (not illustrated) is a storage means provided in the information processing apparatus 100 and stores various kinds of data, such as, for example, data of the information processing method according to the present embodiment, such as the dictionary data and the calibration information, image data indicating the polarization image, and an application.

Examples of the storage unit (not illustrated) described herein include a magnetic recording medium such as a hard disk, a non-volatile memory such as a flash memory, and the like. Further, the storage unit (not illustrated) may be detachably mounted on the information processing apparatus 100.

Examples of the communication unit (not illustrated) include a communication interface described below. Further, examples of the operation unit (not illustrated) includes an operation input device described below, and examples of the display unit (not illustrated) includes a display device described below.

[An Example of a Hardware Configuration of the Information Processing Apparatus 100]

Figure 17:
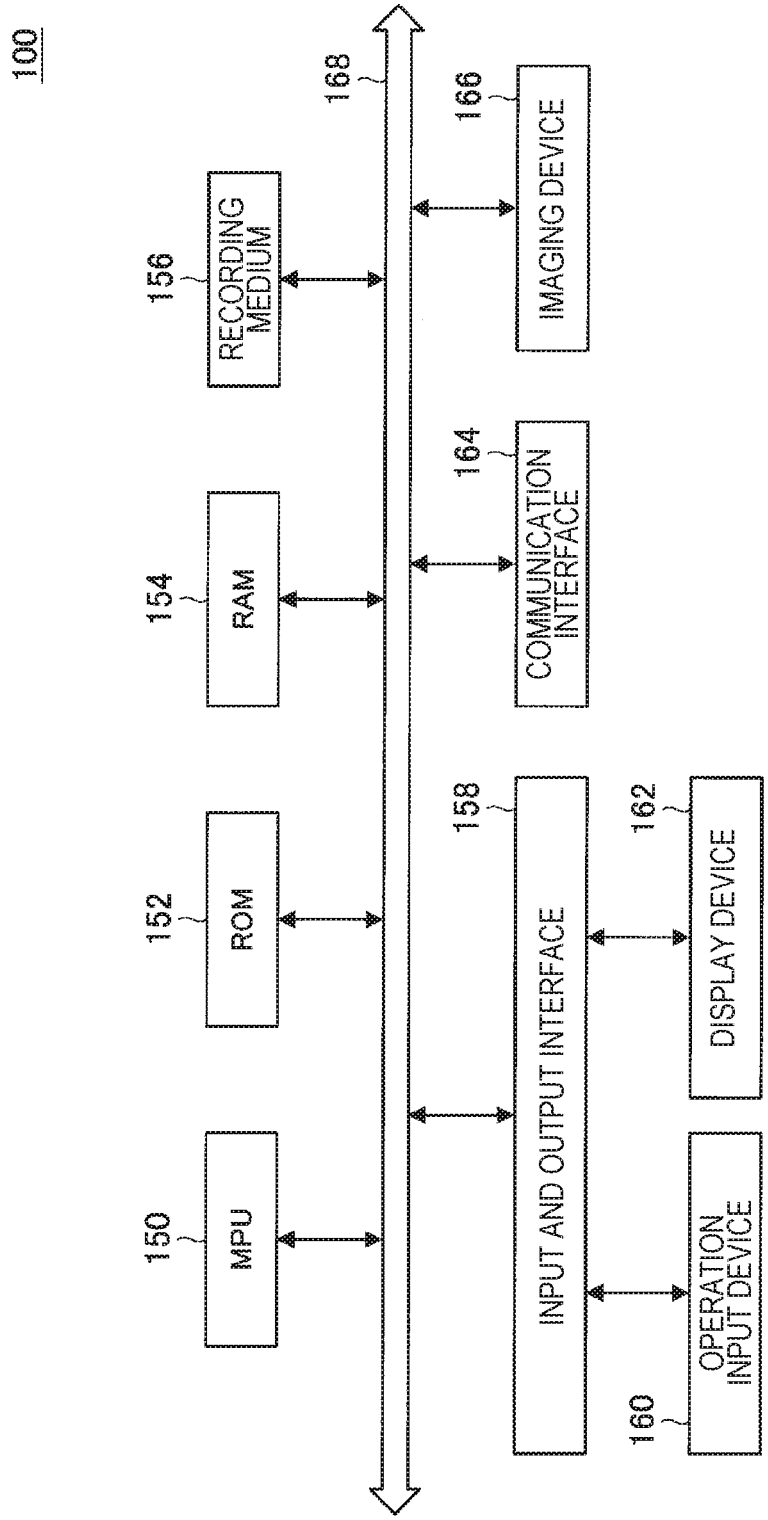
FIG. 17 is an illustration that explains an example of a hardware configuration of the information processing apparatus according to the present embodiment.

FIG. 17 is an illustration that explains an example of a hardware configuration of the information processing apparatus 100 according to the present embodiment. The information processing apparatus 100 includes, for example, an MPU 150, a ROM 152, a RAM 154, a recording medium 156, an input and output interface 158, an operation input device 160, a display device 162, a communication interface 164, and an imaging device 166. Further, the information processing apparatus 100 connects the constituent elements, for example, by a bus 168 serving as a data transmission path.

The MPU 150 includes, for example, one or more processors configured from an arithmetic circuit such as a micro processing unit (MPU), various processing circuits, and the like, and functions as the control unit 104 that controls the entire information processing apparatus 100. Further, the MPU 150 serves as, for example, a processing unit 110 described below in the information processing apparatus 100.

The ROM 152 stores a program used by the MPU 150, control data such as an arithmetic parameter, and the like. The RAM 154 temporarily stores, for example, the program executed by the MPU 150 and the like.

The recording medium 156 functions as the storage unit (not illustrated) and stores various kinds of data, such as, for example, data of the information processing method according to the present embodiment, such as the dictionary data and the calibration information, image data indicating the polarization image, and an application.

Examples of the recording medium 156 include a magnetic recording medium such as a hard disk, a non-volatile memory such as a flash memory, and the like. Further, the recording medium 156 may be detachably mounted on the information processing apparatus 100.

The input and output interface 158 connects, for example, the operation input device 160 and the display device 162. The operation input device 160 functions as the operation unit (not illustrated) and the display device 162 functions as the display unit (not illustrated). Examples of the input and output interface 158 described herein include a universal serial bus (USB) terminal, a digital visual interface (DVI) terminal, a high-definition multimedia interface (HDMI, registered trademark) terminal, various processing circuits, and the like.

The operation input device 160 is, for example, arranged on the information processing apparatus 100 and connected to the input and output interface 158 inside the information processing apparatus 100. Examples of the operation input device 160 include a button, a direction key, a rotation type selector such as a jog dial, a combination thereof, and the like.

The display device 162 is, for example, arranged on the information processing apparatus 100 and connected to the input and output interface 158 inside the information processing apparatus 100. Examples of the display device 162 include a liquid crystal display (LCD), an organic electroluminescence (EL) display (also called an organic light emitting diode (OLED) display), and the like.

Note that, needless to say, the input and output interface 158 can be connected to an external device, such as an operation input device (e.g., a keyboard, a mouse, etc.), a display device, and an imaging device, serving as an external device of the information processing apparatus 100. Further, the display device 162 may be a device that can perform a display while allowing user operation, such as, for example, a touch screen device.

The communication interface 164 is a communication means provided to the information processing apparatus 100 and functions as the communication unit (not illustrated) for performing wireless or wired communication with an external device such as an external imaging device and an external display device and an external device such as a server via a network (or directly). Examples of the communication interface 164 include a communication antenna and a radio frequency (RF) circuit (wireless communication), an IEEE 802.15.1 port and a transmission and reception circuit (wireless communication), an IEEE 802.11 port and a transmission and reception circuit (wireless communication), a local area network (LAN) terminal and a transmission and reception circuit (wired communication), and the like. Further, the communication unit (not illustrated) may be configured to support any standard capable of performing communication, such as a universal serial bus (USB) terminal and a transmission and reception circuit, or may adopt any configuration capable of communicating with an external device via a network.

Further, examples of the network according to the present embodiment include a wired network such as a LAN and a wide area network (WAN), a wireless network such as a wireless local area network (WLAN) and a wireless wide area network (WWAN) via a base station, an internet using a communication protocol such as a transmission control protocol/internet protocol (TCP/IP), and the like.

The imaging device 166 is an imaging means provided to the information processing apparatus 100 and functions as the imaging unit 102 that generates the polarization image by imaging. The information processing apparatus 100 including the imaging device 166 can perform the processes of the information processing method according to the present embodiment, for example, on the basis of the polarization image generated by imaging with the imaging device 166.

The imaging device 166 is configured by including, for example, lens/imaging element and a signal processing circuit. The lens/imaging element is configured from, for example, a lens of optical system and an image sensor employing a plurality of imaging elements such as a complementary metal oxide semiconductor (CMOS) and a charge-coupled device (CCD). The signal processing circuit includes, for example, an automatic gain control (AGC) circuit and an analog to digital converter (ADC) and converts an analogue signal generated by the imaging element into a digital signal (the image data). Further, signal processing circuit performs various processes related to, for example, RAW development.

The information processing apparatus 100 performs the processes of the information processing method according to the present embodiment, for example, by having a configuration shown FIG. 17. Note that the hardware configuration of the information processing apparatus 100 according to the present embodiment is not limited to the configuration shown FIG. 17.

For example, in a case where the processes of the information processing method according to the present embodiment are performed on the basis of the polarization image imaged with an external imaging device, the information processing apparatus 100 does not need to include the imaging device 166.

Further, for example, in a case where the information processing apparatus 100 is configured to perform the processes on a stand-alone basis or performs the communication using an external communication device, the information processing apparatus 100 does not need to include the communication interface 164. Further, the information processing apparatus 100 may be configured without one or more of the recording medium 156, the operation input device 160, and the display device 162.

Again, referring to FIG. 16, an example of the configuration of the information processing apparatus 100 according to the present embodiment will be explained. The imaging unit 102 generates the polarization image by imaging. Examples of the imaging unit 102 include the imaging device 166.

The control unit 104 is configured from, for example, an MPU and the like and has a function in controlling the entire information processing apparatus 100. Further, the control unit 104 includes, for example, the processing unit 110 and has a function in initiatively performing the processes of the information processing method according to the present embodiment.

The processing unit 11, for example, has a function in initiatively performing the detection processes according to the present embodiment and detects the gaze of the detection object on the basis of the normal line obtained from the polarization image. The processing unit 110 detects the gaze of the detection object on the basis of the polarization image, for example, by performing the processes shown in FIG. 5.

Further, the processing unit 110 can perform, for example, one or more of the other detection processes of the first example in (I) to the other detection processes of the fourth example in (IV) described above.

In the case where the processing unit 110 can perform one or more of the other detection processes of the first example in (I) to the other detection processes of the fourth example in (IV) described above, the information processing apparatus 100, for example, further includes a function of performing one or more of the other detection processes of the first example in (I) to the other detection processes of the fourth example in (IV) described above in addition to the function of performing the detection processes according to the present embodiment.

The information processing apparatus 100 performs the processes of the information processing method according to the present embodiment (e.g., the "detection processes" or the "detection processes and other detection processes"), for example, by having the configuration shown in FIG. 16. Thus, the information processing apparatus 100 can detect the gaze of the gaze-detection subject, for example, by having the configuration shown in FIG. 16.

Further, the information processing apparatus 100 can achieve the effects achieved by performing the processes of the information processing method according to the present embodiment described above, for example, by having the configuration shown in FIG. 16.

Note that the configuration of the information processing apparatus according to the present embodiment is not limited to the configuration shown in FIG. 16.

For example, the information processing apparatus according to the present embodiment can include the processing unit 110 shown in FIG. 16 separately from the control unit 104 (e.g., the processing unit 110 is achieved by a separate processing circuit). Further, the processing unit 110 may be achieved by a plurality of the processing circuits and each function may be separately performed by the plurality of the processing circuits.

Further, the configuration for achieving the processes of the information processing method according to the present embodiment is not limited to the configuration shown in FIG. 16 and can be modified depending on how the processes of the information processing method according to the present embodiment are divided.

Further, for example, in the case where the processing unit 110 has the function of performing one or more of the other detection processes of the first example in (I) to the other detection processes of the fourth example in (IV) described above, the information processing apparatus according to the present embodiment can be configured without the function of performing the detection processes according to the present embodiment.

Further, for example, in a case where the processes of the information processing method according to the present embodiment are performed on the basis of the polarization image imaged with an external imaging device having a function and configuration similar to those of the imaging unit 102, the information processing apparatus according to the present embodiment does not need to include the imaging unit 102.

In the foregoing, the information processing apparatus has been described as an example of the present embodiment, however, the present embodiment is not limited thereto. For example, the present embodiment can be applied to various apparatuses that can perform the processes of the information processing method according to the present embodiment, such as a "wearable device used by mounting on the head of the detection object such as an eyewear shown in FIG. 1A", a "computer such as a PC and a server", a "communication device such as a smartphone", a "display device", a "tablet type device", a "game machine", and a "mobile object such as an automobile". Further, for example, the present embodiment can be also applied to a processing IC that can be incorporated into the above apparatuses.

Further, the information processing apparatus according to the present embodiment can be applied to various use cases to which the gaze detection can be applied, for example, such as those described below. Note that, needless to say, the use cases to which the information processing apparatus according to the present embodiment can be applied are not limited to those described below. Further, in the use cases such as the following, the information processing apparatus according to the present embodiment may or may not include the display device as described above.

In a medical field, an operation input of a medical apparatus may be performed by detecting the gaze of a medical professional (an example of the detection object) such as a medical doctor. In this manner, the medical professional such as a medical doctor can operate the medical apparatus without using his/her hand, thereby, for example, making it possible to increase an efficiency and success rate of a surgical operation. Further, using a device operable by the gaze detection can reduce the difficulty in living activity for a physically handicapped patient (an example of the detection object) or the like.

During an operation of a mobile object such as an automobile, detecting the gaze of a driver (an example of the detection object), for example, makes it possible to operate a navigation system displayed on a display screen of a display device and provide information related to an object the driver gazes, such as a building. The information related to the object such as a building may be, for example, displayed on the display screen of the display device or notified to the driver by voice. This allows the driver to operate the device without using his/her hand, thereby making it possible to reduce a possibility of inattentive driving and increase driving safety. Further, for example, a driving level of the driver can be determined by recording a gaze destination of the driver in a recording medium and comparing the recorded gaze destination of the driver and predetermined gaze data of a user model. Further, for example, attention of the driver may be determined by comparing the recorded gaze destination of the driver and the predetermined gaze data of a user model to issue a warning to the driver by voice or the like.

In sports, for example, a right form may be proposed to a sport player (an example of the detection object) by detecting the gaze the sport player.

In an advertisement marketing, for example, a commodity to be recommended to a marketing target (an example of the detection object) may be proposed by detecting the gaze of the marketing target.

In agriculture, by detecting a person engaged in agriculture (an example of the detection object), for example, supplementary information related to a condition of a crop to which the person engaged in agriculture pays attention, or the like, may be provided through a display on a display screen of a display device or the like.

In a livestock industry, for example, a gaze detection result of an animal (an example of the detection object) may be used for a health care or the like of the animal. For example, timing of delivery, poor health, or the like of the animal can be estimated by comparing the detected gaze and model data of the gaze. Further, a sanitary condition in a stable may be estimated from the gaze detection result of the animal in the stable.

Further, the information processing apparatus according to the present embodiment may be applied to a processing system built on the basis of a network connection (or communication between devices) such as, for example, cloud computing. Examples of the processing system in which the processes of the information processing method according to the present embodiment are performed include a "system in which a part of the processes of the information processing method according to the present embodiment are performed by one device constituting the processing system and the processes, other than the part of the processes, of the information processing method according to the present embodiment are performed by other devices constituting the processing system".

(A Program According to the Present Embodiment)

A program causing a computer to function as the information processing apparatus according to the present embodiment (e.g., a program by which the processes of the information processing method according to the present embodiment, such as the "detection processes" or the "detection processes and other detection processes", can be executed) is executed by a processor or the like in the computer to make it possible to detect the gaze of the gaze-detection subject.

Further, the program causing the computer to function as the information processing apparatus according to the present embodiment is executed by the processor or the like in the computer to make it possible to achieve the effects achieved by the processes of the information processing method according to the present embodiment described above (e.g., the effects or the like achieved by the other detection processes of the information processing method according to the present embodiment described above).

Further, the program causing the computer to function as the information processing apparatus according to a modification of the present embodiment, the device having the function of performing one or more of the other detection processes of the first example in (I) to the other detection processes of the fourth example in (IV) described above, but not the function of performing the detection processes according to the present embodiment, is executed by the processor or the like in the computer to make it possible to achieve the effects achieved by the other detection processes of the information processing method according to the present embodiment described above.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the foregoing description, the program (a computer program) causing the computer to function as the information processing apparatus according to the present embodiment is provided. Further, the present embodiment can also provide a recording medium in which the above program is stored.

The above configurations are described as an example of the present embodiment and, needless to say, pertain to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including
a processing unit that detects a gaze of a gaze-detection subject on a basis of a polarization image in which an eye of the detection object is imaged.

(2)

The information processing apparatus according to (1), in which the processing unit estimates a center position of a cornea in the eye on a basis of the polarization image to detect the gaze of the detection object.

(3)

The information processing apparatus according to (2), in which the processing unit estimates the center position of the cornea on a basis of a position of a pupil in the eye detected on a basis of the polarization image, and the polarization image.

(4)

The information processing apparatus according to any one of (1) to (4), in which the processing unit detects the gaze of the detection object on a basis of a normal line obtained from the polarization image.

(5)

The information processing apparatus according to (4), in which the processing unit estimates a center position of a cornea in the eye on a basis of the normal line obtained from the polarization image to detect the gaze of the detection object.

(6)

The information processing apparatus according to (5), in which the processing unit estimates the center position of the cornea on a basis of a normal line corresponding to the cornea estimated on a basis of the polarization image.

(7)

The information processing apparatus according to (6), in which the processing unit estimates the normal line corresponding to the cornea on a basis of a position of a pupil in the eye detected on a basis of the polarization image, and the normal line obtained from the polarization image.

(8)

The information processing apparatus according to any one of (5) to (7), in which the processing unit
estimates a center position of a pupil in the eye on a basis of the estimated center position of the cornea and a radius of the cornea, and
obtains an optical axis vector corresponding to the gaze of the detection object on a basis of the estimated center position of the cornea and the estimated center position of the pupil to detect the gaze of the detection object.

(9)

The information processing apparatus according to (7), in which the processing unit specifies the normal line corresponding to the cornea among a plurality of normal lines obtained from the polarization image on a basis of the detected position of the pupil in the eye.

(10)

The information processing apparatus according to (9), in which the processing unit estimates the normal line corresponding to the cornea on a basis of the detected position of the pupil in the eye and a shape of the cornea.

(11)

The information processing apparatus according to (8), in which the processing unit corrects the optical axis vector on a basis of calibration information to detect the gaze of the detection object.

(12)

The information processing apparatus according to (1), in which the processing unit detects the gaze of the detection object on a basis of normal lines obtained from a first polarization image and a second polarization image constituting a stereo image.

(13)

The information processing apparatus according to (12), in which the processing unit estimates a center position of a cornea in the eye on a basis of the normal lines obtained from the first polarization image and the second polarization image to detect the gaze of the detection object.

(14)

The information processing apparatus according to (13), in which the processing unit estimates a radius of the cornea on a basis of the normal lines obtained from the first polarization image and the second polarization image and parallax, and estimates the center position of the cornea in the eye on a basis of the estimated radius of the cornea.

(15)

The information processing apparatus according to any one of (1) to (14), in which the processing unit acquires the polarization image from an imaging device that is fixed in a predetermined position with respect to the detection object.

(16)

The information processing apparatus according to any one of (1) to (14), in which the processing unit acquires the polarization image from an imaging device that is fixed in a predetermined position with respect to a display device.

(17)

The information processing apparatus according to any one of (1) to (16), further including:
 a display device; and
 an imaging device that acquires the polarization image, the imaging device being fixed with respect to the display device.

(18)

The information processing apparatus according to (17), in which the display device and the imaging device constitute a wearable device wearable on the detection object.

(19)

An information processing method that is executed by an information processing apparatus, including
 a step of detecting a gaze of a gaze-detection subject on a basis of a polarization image in which an eye of the detection object is imaged.

(20)

A program that causes a computer to achieve
 a function of detecting a gaze of a gaze-detection subject on a basis of a polarization image in which an eye of the detection object is imaged.

REFERENCE SIGNS LIST 100 information processing apparatus
102 imaging unit
104 control unit
110 processing unit

The invention claimed is:

1. An information processing apparatus, comprising:
 a processor configured to:
  estimate a center position of a cornea in an eye of a subject based on a normal line obtained from a polarization image of the eye of the subject;
  estimate a center position of a pupil in the eye based on the estimated center position of the cornea and a radius of the cornea;
  obtain an optical axis vector corresponding to a gaze of the subject based on the estimated center position of the cornea and the estimated center position of the pupil; and
  detect the gaze of the subject based on the optical axis vector.

2. The information processing apparatus according to claim 1, wherein the processor is further configured to estimate the center position of the cornea based on a position of the pupil in the eye and the polarization image.

3. The information processing apparatus according to claim 1, wherein the processor is further configured to detect the gaze of the subject based on the normal line obtained from the polarization image.

4. The information processing apparatus according to claim 1, wherein the center position of the cornea is estimated based on the normal line corresponding to the cornea.

5. The information processing apparatus according to claim 4, wherein the processor is further configured to estimate the normal line corresponding to the cornea based on a position of the pupil in the eye, and the normal line obtained from the polarization image.

6. The information processing apparatus according to claim 5, wherein the processor is further configured to specify the normal line corresponding to the cornea among a plurality of normal lines obtained from the polarization image based on the position of the pupil in the eye.

7. The information processing apparatus according to claim 6, wherein the processor is further configured to estimate the normal line corresponding to the cornea based on the position of the pupil in the eye and a shape of the cornea.

8. The information processing apparatus according to claim 1, wherein the processor is further configured to correct the optical axis vector based on calibration information.

9. The information processing apparatus according to claim 1, wherein the processor is further configured to detect the gaze of the subject based on normal lines obtained from a first polarization image and a second polarization image constituting a stereo image.

10. The information processing apparatus according to claim 9, wherein the processor is further configured to estimate the center position of the cornea in the eye based on the normal lines obtained from the first polarization image and the second polarization image.

11. The information processing apparatus according to claim 10, wherein the processor is further configured to:
 estimate the radius of the cornea based on the normal lines obtained from the first polarization image and the second polarization image and parallax, and
 estimate the center position of the cornea in the eye based on the estimated radius of the cornea.

12. The information processing apparatus according to claim 1, wherein the processor is further configured to acquire the polarization image from an imaging device that is fixed in a determined position with respect to the subject.

13. The information processing apparatus according to claim 1, wherein the processor is further configured to acquire the polarization image from an imaging device that is fixed in a determined position with respect to a display device.

14. The information processing apparatus according to claim 1, further comprising:
 a display device; and
 an imaging device configured to acquire the polarization image, wherein the imaging device is fixed with respect to the display device.

15. The information processing apparatus according to claim 14, wherein the display device and the imaging device constitute a wearable device wearable by the subject.

16. The information processing apparatus according to claim 1, wherein the processor is further configured to:
 determine an inner product of the normal line of the polarization image and a normal line of a sphere re-projected onto the polarization image; and
 determine the gaze of the eye of the subject based on the determined inner product.

17. An information processing method, comprising:
in an information processing apparatus:
- estimating a center position of a cornea in an eye of a subject based on a normal line obtained from a polarization image of the eye of the subject;
- estimating a center position of a pupil in the eye based on the estimated center position of the cornea and a radius of the cornea;
- obtaining an optical axis vector corresponding to a gaze of the subject based on the estimated center position of the cornea and the estimated center position of the pupil; and
- detecting the gaze of the subject based on the optical axis vector.

18. A non-transitory computer-readable medium having stored thereon computer-executable instructions, which when executed by a processor, cause the processor to execute operations, the operations comprising:
- estimating a center position of a cornea in an eye of a subject based on a normal line obtained from a polarization image of the eye of the subject;
- estimating a center position of a pupil in the eye based on the estimated center position of the cornea and a radius of the cornea;
- obtaining an optical axis vector corresponding to a gaze of the subject based on the estimated center position of the cornea and the estimated center position of the pupil; and
- detecting the gaze of the subject based on the optical axis vector.

* * * * *